US012576138B2

(12) United States Patent
Meinel et al.

(10) Patent No.: US 12,576,138 B2
(45) Date of Patent: *Mar. 17, 2026

(54) COMPOUNDS AND METHODS FOR THE IMMOBILIZATION OF MYOSTATIN-INHIBITORS ON THE EXTRACELLULAR MATRIX BY TRANSGLUTAMINASE

(71) Applicant: JULIUS-MAXIMILIANS-UNIVERSITÄT WÜRZBURG, Würzburg (DE)

(72) Inventors: Lorenz Meinel, Würzburg (DE); Tessa Lühmann, Würzburg (DE); Alexandra Braun, Gerbrunn (DE)

(73) Assignee: Julius-Maximilians-Universität Würzburg, Würzburg (DE)

( * ) Notice: Subject to any disclaimer, the term of this patent is extended or adjusted under 35 U.S.C. 154(b) by 1167 days.

This patent is subject to a terminal disclaimer.

(21) Appl. No.: 17/047,851

(22) PCT Filed: May 17, 2019

(86) PCT No.: PCT/EP2019/062830
§ 371 (c)(1),
(2) Date: Oct. 15, 2020

(87) PCT Pub. No.: WO2019/219923
PCT Pub. Date: Nov. 21, 2019

(65) Prior Publication Data
US 2021/0138043 A1 May 13, 2021

(30) Foreign Application Priority Data
May 18, 2018 (EP) .................................... 18173245

(51) Int. Cl.
| | |
|---|---|
| *A61P 17/02* | (2006.01) |
| *A61K 9/00* | (2006.01) |
| *A61K 9/06* | (2006.01) |
| *A61K 38/10* | (2006.01) |
| *A61K 38/30* | (2006.01) |
| *A61K 38/45* | (2006.01) |
| *A61K 39/395* | (2006.01) |
| *A61K 47/65* | (2017.01) |
| *A61L 15/40* | (2006.01) |
| *A61L 15/60* | (2006.01) |
| *A61L 27/22* | (2006.01) |
| *A61L 27/24* | (2006.01) |
| *A61L 27/36* | (2006.01) |
| *A61L 27/50* | (2006.01) |
| *A61L 27/54* | (2006.01) |
| *A61L 27/56* | (2006.01) |
| *A61L 31/04* | (2006.01) |
| *A61L 31/16* | (2006.01) |

(52) U.S. Cl.
CPC ............ *A61K 38/45* (2013.01); *A61K 9/0014* (2013.01); *A61K 9/0024* (2013.01); *A61K 9/06* (2013.01); *A61K 38/10* (2013.01); *A61K 38/30* (2013.01); *A61K 39/3955* (2013.01); *A61K 47/65* (2017.08); *A61L 15/40* (2013.01); *A61L 15/60* (2013.01); *A61L 27/225* (2013.01); *A61L 27/227* (2013.01); *A61L 27/24* (2013.01); *A61L 27/3633* (2013.01); *A61L 27/365* (2013.01); *A61L 27/507* (2013.01); *A61L 27/54* (2013.01); *A61L 27/56* (2013.01); *A61L 31/047* (2013.01); *A61L 31/16* (2013.01); *A61P 17/02* (2018.01)

(58) Field of Classification Search
CPC .... A61K 38/45; A61K 9/0014; A61K 9/0024; A61K 9/06; A61K 38/10; A61K 38/30; A61K 39/3955; A61K 47/65; A61K 38/00; A61L 15/40; A61L 15/60; A61L 27/225; A61L 27/227; A61L 27/24; A61L 27/3633; A61L 27/365; A61L 27/507; A61L 27/54; A61L 27/56; A61L 31/047; A61L 31/16; A61P 17/02; C12N 9/1044; C12Y 203/02013; C07K 2319/01; C07K 2319/70; C07K 14/65; C07K 14/475
See application file for complete search history.

(56) References Cited

U.S. PATENT DOCUMENTS

| | | | |
|---|---|---|---|
| 6,607,740 B1 | 8/2003 | Hubbell et al. | |
| 2020/0283494 A1* | 9/2020 | Braun .................. | C12N 5/0697 |

FOREIGN PATENT DOCUMENTS

| | | |
|---|---|---|
| EP | 2241575 A1 | 10/2010 |
| WO | 1998043686 A1 | 10/1998 |

(Continued)

OTHER PUBLICATIONS

Braun et al., Matrix Metalloproteinase Responsive Delivery of Myostatin Inhibitors, Pharmacological Research, vol. 34, p. 58-72. (Year: 2016).*

(Continued)

*Primary Examiner* — Adam Weidner
*Assistant Examiner* — Tiffany M Gough
(74) *Attorney, Agent, or Firm* — SALIWANCHIK, LLOYD & EISENSCHENK

(57) ABSTRACT

The present invention relates to compounds and their use in the treatment of lesions, in tissue regeneration and/or tissue engineering. The compounds act as substrates for enzymes having transglutaminase activity and are suitable for their immobilization and/or attached therapeutic or diagnostic molecules on extracellular matrix (ECM) or synthetic ECM-derived materials, in particular for the immobilization of myostatin inhibitors.

11 Claims, 8 Drawing Sheets

Specification includes a Sequence Listing.

(56) References Cited

FOREIGN PATENT DOCUMENTS

| | | | |
|---|---|---|---|
| WO | 2004058988 | A2 | 7/2004 |
| WO | 2008054826 | A2 | 5/2008 |
| WO | 2010105302 | A1 | 9/2010 |
| WO | 2014144903 | A1 | 9/2014 |

OTHER PUBLICATIONS

Lorentz, Kirsten M. et al. "Engineered insulin-like growth factor-1 for improved smooth muscle regeneration" Biomaterials, 2012, pp. 494-503, vol. 33.

Sivaramakrishnan, Manaswini et al. "Lysine residues of IGF-I are Substrates for transglutaminases and modulate downstream IGF-I signalling" Biochimica et Biophysica Acta, 2013, pp. 3176-3185, vol. 1833.

Liu, Wei et al. "Myostatin Is a Skeletal Muscle Target of Growth Hormone Anabolie Aetion" The Journal of Climcol Endocrinology & Mctabolisin, 2003, pp. 5490-5496, vol. 88, No. 11.

Shishkin, S.S. et al. "Effects of Myostatin and Other Growth Factors on Cultured Human Cells" Prikladnaa Biohimia I Mikrobiologia Applied Biochemistry Andmicrobio, Nov. 1, 2014, pp. 630-633, vol. 40, No. 6, English abstract on p. 633.

* cited by examiner

U30826WO
Julius-Maximilians-Universität Würzburg

Granulation tissue matrix

MI-D chain

TGase

Myostatin

TGase

Collagen Type III
Glucosaminoglycans
Fibronectin

COMPOUNDS AND METHODS FOR THE IMMOBILIZATION OF MYOSTATIN-INHIBITORS ON THE EXTRACELLULAR MATRIX BY TRANSGLUTAMINASE

CROSS REFERENCE TO RELATED APPLICATIONS

This application is a National Stage Application of International Application Number PCT/EP2019/062830, filed May 17, 2019; which claims priority to European Application No. 18173245.4, filed May 18, 2018.

The Sequence Listing for this application is labeled "SeqList-16Oct20-ST25.txt", which was created on Oct. 16, 2020 and is 3 KB. The entire content is incorporated herein by reference in its entirety.

The present invention relates to compounds and their use in the treatment of lesions, in tissue regeneration and/or tissue engineering. The compounds act as substrates for enzymes having transglutaminase activity and are suitable for their immobilization and/or attached therapeutic molecules on extracellular matrix (ECM) or synthetic ECM-derived materials.

BACKGROUND OF THE INVENTION

Aging, obesity, diabetes, cardiovascular disorders, sensory neuropathies, and autoimmune diseases are multiple causes that delay wound healing and dramatically increase the global burden of chronic wounds. Unfortunately, no generally satisfactory clinical solution for chronic wounds is available today. Providing an effective therapy to heal diabetic foot ulcers, which plague patients as a major diabetes complication, could result in a decrease of the substantial morbidity including amputation and reduction of lifespan and quality of life. To this end, novel biologics are developed and evaluated, mainly based on growth factors, which are key signaling molecules regulating tissue repair and regeneration, including insulin-like growth factor I (IGF-I), vascular endothelial growth factor (VEGF), fibroblast growth factor 2 (FGF-2) and platelet-derived growth factor (PDGF) [3]. However, although a number of growth factors involved in skin repair have been identified, their translation into the clinic has been very limited.

The design of controlled release strategies for dose reduction combined with temporal and spatial dose localization is an ongoing challenge. The extracellular matrix (ECM) plays a fundamental role in coordinating growth factor signaling in vivo, by presenting and releasing them in a highly spatio-temporal controlled manner and by modulating their intracellular signaling.

The process of wound healing is divided into three distinct phases. Firstly, the inflammatory or exudative phase for the detachment of deteriorated tissue and for wound cleaning; Secondly a proliferative phase for the development of granulation tissue; and thirdly a differentiation or regeneration phase for maturation and scar formation. During the proliferation phase—characterized by epithelialization, angiogenesis, granulation tissue formation, and collagen deposition—the damaged ECM is replaced by a provisional fibrin matrix with altered composition compared to healthy skin (mainly constituted of fibrinogen and fibronectin, FIG. 2). During the repair process, granulation tissue is formed with an excessive proportion of collagen type III and increased fibronectin. During the subsequent remodeling phase, the network of elastic fibers reestablished and the matrix reorganizes to reach a composition closer to the initial skin ECM [4].

Wound healing requires the involvement of several distinct TGases to reconstitute tissue integrity damaged by traumatic or pathological injuries [5]. Factor XIIIa—a human transglutaminase activated from factor XIII by thrombin proteolysis during wound healing—is responsible for cross-linking fibrin monomers as an initial response to enclose the wound during injury. In addition, it is involved in the activation of platelets and in the deposition of granulation tissue, representing the first stable repair to a local lesion. TGase is normally secreted into the ECM in insignificant amounts, but following cell insult, stress or cell damage, TGase levels are strongly upregulated due to release of intracellular TGase and activation of externalized TGase in the ECM. Continued stress results in enhanced TGase expression and cell death leading to further release of TGase with the effect of protein crosslinking (mainly fibronectin) for ECM stabilization and promotion of cell adhesion and survival, thereby maintaining tissue integrity [6].

Fibronectin is a 440 kDa extracellular matrix protein that plays major roles in cell adhesion, migration and growth factor storage and has a N-terminal located glutamine residue serving as high-affinity substrate for transglutaminases [9, 10]. FXIIIa shows a high binding affinity for fibronectin and catalyzes covalent cross-linking of matrix proteins and growth factors including IGF-I to fibronectin.

In terms of tissue engineering and drug delivery purposes, transamidation by FXIIIa has already found application in the incorporation of exogenous peptides into fibrin gels, the controllable crosslinking in biological or synthetic hydrogels, and for surface functionalization [7-10]. In these studies, a short synthetic peptide with the sequence FKG is frequently used to modify peptides in order to render them suitable substrates for transglutaminases, but the coupling efficacy is frequently low depending on location of the modification site within the protein, peptide or polymer [8, 9].

Myostatin—a member of the transforming growth factor β (TGF-β) family—is well known for its negative regulatory effect of muscle growth and regeneration and is therefore proposed as a promising target for the treatment of muscle wasting diseases. Besides these effects on muscle regeneration and myogenesis, myostatin inhibition is discussed as potential treatment approach for impaired wound healing, as studies revealed improved circumstances for faster wound healing (increased wound hydration, expression of fibromodulin and TGF-β3), reduction of scarring and improvement of diabetic systemic parameters by myostatin inhibition [11].

Based on these molecular processes during wound healing, a biomimetic strategy was surprisingly and unexpectedly found, wherein transglutaminase—an enzyme physiologically upregulated following tissue injury—was co-delivered together with a myostatin inhibitor for in situ immobilization on fibronectin to facilitate fast and scar-free wound healing.

Further, it was surprisingly and unexpectedly found that said immobilized myostatin inhibitor could be cleaved from the extracellular matrix in response to external stimuli, while retaining its bioactive properties.

Hence, a targeted release of myostatin inhibitor allows a controlled capturing of upregulated myostatin at the wound site and enables immediate and sustained release of said myostatin inhibitor with preserved bioactivity.

Yang et al 2008 disclose peptide M1557 containing the IGF-I D-domain as well three amino acids of the neighboring A-domain (peptide sequence YCAPLKPAKSA). They suggest that Try-60 of the A-domain plays an important role in the binding of IGF-I receptor to the D-domain.

Sivaramakrishan et al. 2013 disclose that the D-domain IGF-I is a substrate for transglutaminases. They disclose that especially the lysine residues of the D-domain are functionally important. Further, Sivaramakrishan et al. 2013 describes the role of transglutaminases in the immobilization of IGF-I to proteins of the extracellular matrix via the D-Domain of IGF-I.

US2009/0136487 discloses the treatment of sarcopenia with a myostatin antagonist.

WO 2004058988 A2 discloses binding agents which inhibit myostatin.

WO2014/097116 discloses stabilized IGF-variants, wherein a mutation prevents their cleavage in serum. Also disclosed are pharmaceutical compositions comprising a combination of these IGF-variants and a myostatin inhibitor. However, WO 2014/097116 does not disclose that the D-domain of IGF-I may be used solely and that the D-domain may be connected to a myostatin inhibitor for immobilization on the extracellular matrix.

In nature, growth factors (GFs) such as TGF-β, VEGF and PDGF are present bound to the ECM, but therapeutic use of such growth factors has focused on application in soluble forms. Thus, GFs are quickly cleared from the treated tissue upon administration. Physiologically, GFs are not only secreted by cells into wound tissue, but they are also sequestered locally by the ECM. The ECM controls the spatiotemporal release of GFs, which makes them highly effective at very low dose and allows proper tissue morphogenesis. In contrast, growth factors delivered in soluble forms underlie limited clinical translation due to safety issues and cost effectiveness and several studies highlight the complex biomolecular interactions between growth factors and ECM proteins dramatically altering the pharmacology of the individual growth factor [4, 12].

Attempting to transfer this natural strategy to a MI and retain it in the ECM at the wound site, we modified the MI with a high-affinity transglutaminase substrate sequence derived from the natural growth factor IGF-I. The lysine residue #68, within the D domain of IGF-I (PLKPAKSA) represents an excellent substrate for Factor XIIIa and tissue TGase and is coupled to the N-terminal glutamine of fibronectin with fast kinetics. We fused this D domain to the C-terminus of the MI—either directly or through an inter-positioned protease cleavable linker—to enhance ECM binding for improved bioactivity and provision of an effective, in situ generated delivery system for skin repair in chronic wound models. Delivering the MI in the context of the strong association of the fused D domain with endogenous ECM is intended to significantly enhance its capacity to induce tissue healing at doses where unmodified myostatin inhibitor is usually not effective. By turning the ECM into a reservoir for MI, locally unregulated myostatin is captured and removed from the wound site to prevent its negative actions on wound healing, such as delayed healing, impaired tissue regeneration and increased fibrosis.

In contrast to most biomaterial-based delivery systems for biologics, this technology is particularly versatile since the MI with high-affinity binding site to fibronectin can be successfully delivered directly into the endogenous ECM, as a carrier-free system. This approach is easily translatable into the clinics by topical co-delivery of TGase and the MI-D chain onto chronic wounds.

The subject-matter of the present invention addresses the need for better means and methods for the treatment of the wounds of different origin, the prevention of worsening of such wounds as well as the prevention or control of non-desirable healing processes of such wounds, e.g., those characterized by excessive scarring, etc.

DETAILED DESCRIPTION OF THE INVENTION

Before disclosing the subject-matter in greater detail, definitions of terms/expressions used herein are provided.

Unless otherwise defined, all technical and scientific terms used herein have the same meaning as commonly understood by one of ordinary skill in the art to which this invention belongs. Although methods and materials similar to those described herein can be used in the practice or testing of the present invention, suitable methods and materials are described below. In addition, the materials, methods, and examples are illustrative only and not intended to be limiting.

Each of the patents, applications and articles cited herein, and each document cited or referenced therein, including during the prosecution of any of the patents and/or applications cited herein ("patent cited documents"), and any manufacturer's instructions or catalogues for any products cited herein or mentioned in any of the references and in any of the patent cited documents, are hereby incorporated herein by reference. Documents incorporated by reference into this text or any teachings therein may be used in the practice of this invention. Documents incorporated by reference into this text are not admitted to be prior art. As used herein, the words "may" and "may be" are to be interpreted in an open-ended, non-restrictive manner. At minimum, "may" and "may be" are to be interpreted as definitively including structure or acts recited.

The articles "a" and "an" are used herein to refer to one or to more than one (i.e. to at least one) of the grammatical object of the article.

Throughout this specification, unless the context requires otherwise, the words "comprise", "comprises" and "comprising" will be understood to imply the inclusion of a stated step or element or group of steps or elements but not the exclusion of any other step or element or group of steps or elements. In one embodiment, the term "comprising" may relate to "consisting of".

Each of the respective terms "biologically active fragment" or "pharmaceutically active fragment" or "therapeutically active fragment" is meant a fragment of a full-length parent polypeptide which fragment retains the activity of the parent polypeptide. A biologically active fragment will therefore have, for example, at least 75% of the activity of the polypeptide according to SEQ ID NO: 1 using the same test conditions to quantify the activity, namely being suitable for incorporation into the extracellular matrix (ECM) or synthetic ECM-derived materials. In preferred embodiments, the fragments maintain the lysine residue at position 6 of SEQ ID NO: 1.

The terms "biologically active fragment" includes deletion variants and peptides comprising an polypeptide according to SEQ ID NO: 1, for example, of at least 4, at least 5, at least 6, at least 7, at least 8, at least 9, at least 10, at least 15, at least 20, and at least 25, least 30 contiguous amino acids, which comprise the above activities. Peptides of this type may be obtained through the application of standard recombinant protein expression techniques or synthesized using conventional liquid or solid phase peptide synthesis techniques. For example, reference may be made to solution synthesis or solid phase peptide synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a polypeptide of the invention with proteinases such as endo-Lys-C, endoArg-C, endoGlu-C and staphylococcus V8-protease. The digested fragments can be purified by, for example, reverse phase high performance liquid chromatographic (RP-HPLC) techniques. A biologically active fragment according to the invention can therefore be the substrate of a transglutaminase, such as mammalian, e.g., human Factor XIIIa, as long as it is capable of being immobilized onto components of the extracellular matrix (ECM), or to transglutaminase substrates e.g. an alpha-2 plasmin inhibitor (a$_2$PI)-derived Q-peptide or a polypeptide that comprises the target sequence for FXIIIa, e.g., a non-natural, for example, a chimeric/fusion polypeptide that in addition to the target sequence comprises further polypeptidic sequence parts that may serve desired biological functions, which may be the adhesion to biological or non-biological materials.

As used herein, the terms "effective amount" when used with reference to a composition of an active compound refers to an amount or dosage sufficient to produce a desired result (e.g., for therapy with the compositions of the present invention). In the case of sustained delivery compositions comprising compounds of the invention, the desired result may be a desired reduction in inflammation and/or an increase in the healing of a lesioned tissues as detectable by visual inspection of newly formed tissue, closing of lesions, absence or reduction of swelling and/or pain, reduced wound size, etc.), for example. More specifically, a "therapeutically effective amount" of an active compound of the invention, is an amount of that particular compound which is sufficient to inhibit, or halt altogether, or ameliorate, heal, alleviate or cure, for some desired period of time, one or more clinically defined pathological processes associated with the condition at issue. The effective amount may vary depending on the specific active compound(s) selected, and a variety of other factors and conditions related to the subject to be treated and the severity of the conditions, e.g., the age, weight and health of the patient as well as dose response curves and toxicity data obtained in preclinical animal work would be among those considered. If the compound(s) is to be contacted with the cells in vitro, one would also design a variety of pre-clinical in vitro studies to assess such parameters as uptake, half-life, dose, toxicity, etc. The determination of an effective amount or a therapeutically effective amount for a given agent is well within the ability of those skilled in the art.

In the context of treating or preventing a condition or achieving an desired biological effect in systems in vitro the use or administration of an effective amount of active to an individual in need of such treatment or prevention/prophylaxis or to the in vitro cell system, either in a single dose or as part of a series, that is effective for treatment or prophylaxis of a condition. The effective amount will vary depending upon the type of environment (e.g., the type and size of lesion, tissue type(s), etc.) and upon the physical condition of the individual to be treated, the formulation of the composition comprising the herein disclosed compounds, the assessment of the medical situation, and other relevant factors.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The terms "pharmaceutically effective", "therapeutically effective", "pharmaceutically active", or "therapeutically active" means that a synthetic compound of the invention so described is determined to have activity that affects a medical parameter or disease state (for example, the size of and/or inflammation and/or pain associated with a tissue lesion).

"Patient" as that term is used herein, refers to the recipient of the treatment. In a specific embodiment, the patient is a mammal, such as a human, canine, murine, feline, bovine, ovine, swine or caprine. In a preferred embodiment, the patient is a human.

Sustained delivery compositions of the present invention are particularly useful for slow release of active agents with short biological half-lives, such as certain macromolecules such as proteins and peptides. As a result, the sustained delivery compositions described herein may also enable the use of alternative routes of administration when the sustained delivery compositions include a therapeutic drug and are administered to a patient for slow release or targeted delivery of the drug to the site requiring therapy. Frequently, therapeutic use of growth factors such as IGF-I has focused on application in soluble forms. Thus, they are rapidly cleared from the treated area after administration thereby restricting therapy due to safety issues and cost effectiveness. The in situ generated delivery system for IGF-I facilitates local IGF-I accumulation and enables spatiotemporal release of the growth factor controlled by natural ECM remodeling processes. Thus, IGF-I is highly effective at very low dose and allows proper tissue morphogenesis with very low toxicity by emulating the natural storage mechanism.

As used herein, the terms "function" or "functional activity" refer to a biological, e.g., enzymatic function.

By "isolated" is meant material that is substantially or essentially free or purified from components that normally accompany it in its native state. For example, the compound according to the invention may be modified subsequent to isolation from their natural or laboratory-produced environment, or they may be used in isolated form in vitro, or as components of devices, compositions, etc.

By "obtained from" is meant that a sample such as, for example, a polypeptide is isolated from, or derived from, a particular source of the host or cells cultured in vitro. For example, the extract can be obtained from a tissue or a biological fluid sample isolated directly from the host. Therefore, the compounds of the present invention may be recombinantly produced or obtained from biological sources and be purified before further use in vitro and/or in vivo.

By "pharmaceutically acceptable carrier" is meant a solid or liquid filler, stabilizer, diluent or encapsulating substance that can be safely used in administration routes when applied to an animal, e.g. a mammal, including humans.

"Therapeutic treatment", and "treatment", refers any type of therapy referred to herein, e.g., treatment of lesions, including the treatment to prevent the deterioration or worsening of such lesions or wounds, or treatment of chronic diseases like rheumatoid arthritis or tendinitis, or for post-operative prevention of inflammation or joint destruction.

The terms "lesions" or "wounds" are understood as any pathologic, inflammatory, painful, exogenously or endogenously caused disturbance of the integrity of a tissue of an organism, e.g., through any disease, surgical intervention, accident (cuts, stabs, burns, etc.), (auto)inflammation, and the like.

The terms "identical" or percent "identity," in the context of two or more polypeptide sequences, refer to two or more sequences or subsequences that are the same or have a specified percentage of amino acid residues that are the same (i.e., 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection (see, e.g., NCBI web site http://www.ncbi.nlm.nih.gov/BLAST/ or the like).

Such sequences are then said to be "substantially identical." The definition also includes sequences that have deletions and/or additions, as well as those that have substitutions. As described below, the preferred algorithms can account for gaps and the like. Preferably, identity exists over a region that is, for example, at least about 4, 5, 6, 7, 8, amino acids in length.

For sequence comparisons of compounds disclosed herein, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

The terms "polypeptide," "peptide" and "protein" are used interchangeably herein to refer to a polymer of amino acid residues. The terms apply also to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" or "derivative" where the alteration results in the substitution of an amino acid, e.g., with a chemically similar amino acid. Conservative substitution tables providing functionally similar amino acids are well known in the art. According to the present invention, modified variants of the compounds of the invention retain the activity of acting as a donor for transglutaminases, preferably FXIIIa, and may be immobilized on a suitable substrate to which it may be crosslinked enzymatically. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (Creighton, Proteins (1984)).

Below, embodiments of the invention are disclosed. When the expression "and/or" is used, this means that each member of a respective list may be analyzed or used individually, or that more than one member of said list may be used. Further, when a list of members is combined with another list or lists of members, this means that each and every possible combination is encompassed by the present invention even if not every combination of the lists is explicitly, i.e. literally disclosed.

EMBODIMENTS OF THE INVENTION

In one embodiment, the invention relates to a synthetic compound suitable for transglutaminase-mediated binding/attachment/incorporation of a therapeutic molecule and/or diagnostic molecule into an extracellular matrix or a synthetic extracellular matrix component, wherein said compound comprises (a) at least one anchor domain, and (b) at least one second domain, wherein said second domain possesses therapeutic and/or preventive and/or diagnostic activity, wherein said anchor domain is selected from the group comprising:

i. the D domain of Insulin Growth Factor-1 (IGF-I) as depicted in SEQ ID NO: 1, ii. a derivative of i) having at least 50% identity with SEQ ID NO: 1, iii. a fragment of i) or ii), wherein said fragment comprises at least the four C-terminal amino acid residues depicted in SEQ ID NO: 1, or a fragment comprising the at least five, or a fragment comprising the at least six, or a fragment comprising the at least seven, or a derivate thereof having at least 75% identity to the amino acid sequences depicted in SEQ ID NO: 1, and wherein said second domain is directly or indirectly linked to any of the anchor domains referred to in i) to iii), and wherein said second domain comprises or consists of a molecule that inhibits/reduces/suppresses the activity of myostatin, preferably of mammalian myostatin, in particular of human myostatin. In one embodiment, a molecule that inhibits and/or reduces and/or suppresses the activity of myostatin is a myostatin inhibitor (MI). In one embodiment, said second domain comprises or consists of a myostatin inhibitor. In one embodiment, said myostatin inhibitor comprises an amino acid sequence as defined in SEQ ID NO. 12.

In one embodiment, the term "therapeutic molecule" relates to an agent having a therapeutic and/or preventive effect on any of the pathological conditions disclosed herein, and preferably relates to a myostatin inhibitor. In one embodiment, the term "therapeutic or preventive agent", as used herein, relates to a medicament.

In one embodiment, the term "diagnostic molecule" relates to a marker molecule which indicates ECM remodeling and/or protease activity. A diagnostic molecule allows for the monitoring of the presence of the MI either bound to the ECM or upon release during the therapeutic intervention and/or during the therapeutic measures taken with the herein disclosed compounds. A released diagnostic molecule may be labelled and detected in bodily fluid such as blood. In one embodiment, a synthetic compound of the present invention comprising a diagnostic molecule may be used for diagnostic monitoring in vitro and/or in vivo.

The interaction between the molecule inhibiting myostatin and myostatin itself may be measured in vitro using Surface Plasmon Resonance measurements, Isothermal titration calorimetry (ITC), etc. Assays for the inactivation, reduction or suppression of myostatin activity may be performed in vitro in cell culture, e.g., using the activity assay disclosed in Example 2.

The extracellular matrix substrate is preferably a target for human FXIIIa and may be fibronectin or a suitable derivative or fragment thereof that maintains its activity of serving as a target for the immobilization of the synthetic compounds as defined herein. The target may be modified with a glutamine substrate, such as NQEQVSPL (SEQ ID NO: 11).

In embodiments of the invention, the second domain comprises or consists of a molecule that inhibits/reduces/suppresses the activity of myostatin, preferably of mammalian myostatin, in particular of human myostatin, and wherein a diagnostic molecule may be detected either subsequent to its binding to the extracellular matrix or when it is released therefrom, optionally still bound to the MI. It is possible that the diagnostic molecule is bound to the ECM, similarly to the MI, but may be released therefrom, thereby demonstrating and at least partially influenced by the ECM remodeling/protease activity. In one embodiment, a synthetic compound of the present invention comprising a myostatin inhibitor domain is bound to an extracellular matrix or a synthetic extracellular matrix component, and an enzymatic reaction, such as an enzymatic reaction occurring during extracellular matrix remodeling, is necessary to release said myostatin inhibitor domain. In one embodiment, a synthetic compound of the present invention bound to an extracellular matrix or a synthetic extracellular matrix component is not releasable by desorption.

Further, it is possible to attach the diagnostic molecule to the MI and detect free MI or the complex comprising MI and myostatin. The released diagnostic moiety may be labelled and detected in bodily fluid such as blood. Respective molecules allow for the monitoring of the (continued) presence of the MI either bound to the ECM or upon release during the therapeutic intervention and/or during the therapeutic measures taken with the herein disclosed compounds. In one embodiment, the binding, preferably the covalent binding, of a synthetic compound of the present invention to an extracellular matrix or a synthetic extracellular matrix component is mediated by transglutaminase. In one embodiment, said synthetic compound preferably binds to fibronectin within an extracellular matrix or a synthetic extracellular matrix component.

As used herein, the term "inhibits/reduces/suppresses the activity of myostatin" means that the respective molecule, i.e. the myostatin inhibitor (MI) is capable of negatively influencing the activity of myostatin. For example, when the "normal" (i.e., not inhibited, reduced or suppressed activity) is set at 100%, the MI is capable of lowering the activity, e.g., by at least 5%, 10%, 20% 30% 40% 50% 60% 70%, 75%, 80%, 85%, 90%, or 95%, or more, as may be determined using the assay described in Example 2 or any other suitable assay.

As used herein, the terms "therapeutic and/or preventive activity" mean that the second domain is suitable for the treatment and/or prevention of pathological conditions as defined herein, wherein the inhibition, reduction of activity or concentration, or suppression of MI activity can be beneficial. Pathological conditions, as used herein, may be diseases, disease symptoms, disorders, etc. that would benefit from a therapeutic or preventive intervention that aims the restoration of tissue (tissue repair in its broadest sense) as defined throughout this disclosure, such as the treatment of wounds or lesions, or the prevention of a worsening thereof or the prevention of non-desirable, e.g., excessive metabolic activities, e.g., excessive scarring, connective tissue growth, and/or fibrosis. In one embodiment, the term "therapeutic and/or preventive activity" relates to the activity of a myostatin inhibitor.

The expression "at least one second domain" means that the synthetic compound may comprise more than the anchor domain and the second domain. Such further or additional domains may be identical to the second domain, or they may be functional variants thereof, or they may have a different function, preferably, a therapeutic or preventive or indicative function that can be selected according to the pathological condition that would benefit from such function. Indicative function means that a given domain can be detected using known diagnostic methods, e.g., by measuring the concentration at a given time-point or more than one time-point (e.g., in a monitoring of the progress of the treated pathological condition), for example, using fluorescence-measurements, color-measurements, light- or radioactivity measurements, and other methods known in the art of detecting molecules of interest.

Accordingly, in other embodiments of the above embodiments, the synthetic compound comprises more than one "second domain", i.e., a third, fourth, fifth, or further domain that may possess essentially the same therapeutic and/or preventive activity as the so-called second domain. The domains may be slightly different, or may comprise the second domain as defined above, and further domains possess different therapeutic and/or preventive activities, e.g., act as growth factors, cytokines, anti-inflammatory agents, etc.

In other embodiments of the above embodiment, the synthetic compound is preferably proteinaceous, that is, it comprises or consists essentially of amino acids. In one embodiment, the terms "synthetic" and/or "artificial" preferably relate to a property of a product, such as a compound, an extracellular matrix component, or an artificial tissue, indicating that said product is made or produced by human beings rather than occurring naturally, wherein it may relate to a copy of something natural. A synthetic and/or artificial product such as a synthetic compound, a synthetic extracellular matrix component, or an artificial tissue of the present invention may comprise components of natural origin.

In other embodiments of the above embodiments, the synthetic compound according to the preceding embodiments is for use as therapeutic or preventive agent.

In other embodiments of the above embodiments, the synthetic compound according to the preceding embodiments, wherein the second domain is selected from the group comprising a binder of myostatin, preferably an antibody, or an antibody fragment, or an antibody derivative, an aptamer, a non-Ig-scaffold, an antagonist, a myostatin inhibitor/suppressor, a polypeptide or a peptide/protein-polymer conjugate, e.g., an antibody-drug conjugate having MI activity or binding to myostatin, and the natural inhibitor follistatin. In one embodiment, said second domain is a myostatin inhibitor. In one embodiment, the second domain comprises an amino acid sequence as defined in SEQ ID NO. 12 or a functional derivative thereof, wherein, preferably, said amino acid sequence of SEQ ID NO. 12 and/or said functional derivative have a direct inhibitory activity on myostatin. In one embodiment, the term "direct inhibitory activity on myostatin" relates to an inhibitory effect on myostatin which acts on myostatin directly and which does not relate to an indirect effect on myostatin such as via an activation of an anabolic signaling pathway. In one embodiment, the second domain preferably comprises an amino acid sequence as defined in SEQ ID NO. 12.

As used herein, an antibody is a protein including one or more polypeptides substantially encoded by immunoglobulin genes that specifically binds an antigen. The recognized immunoglobulin genes include the kappa, lambda, alpha (IgA), gamma (IgG1, IgG2, IgG3, and IgG4), delta (IgD), epsilon (IgE) and mu (IgM) constant region genes, as well as the myriad immunoglobulin variable region genes. Full-length immunoglobulin light chains are generally about 25 Kd or 214 amino acids in length. Full-length immunoglobulin heavy chains are generally about 50 Kd or 446 amino acid in length. Light chains are encoded by a variable region gene at the NH2-terminus (about 110 amino acids in length) and a kappa or lambda constant region gene at the COOH-terminus. Heavy chains are similarly encoded by a variable region gene (about 116 amino acids in length) and one of the other constant region genes.

The basic structural unit of an antibody is generally a tetramer that consists of two identical pairs of immuno-globulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and (Fab')$_2$, as well as bifunctional hybrid antibodies and single chains (e.g., Lanzavecchiaet al., Eur. J. Immunol. 17:105,1987; Huston et al., Proc. Natl. Acad. Sci. U.S.A., 85:5879-5883, 1988; Bird et al., Science 242:423-426, 1988; Hood et al., Immunology, Benjamin, N.Y., 2nd ed., 1984; Hunkapiller and Hood, Nature 323:15-16,1986). An immunoglobulin light or heavy chain variable region includes a framework region interrupted by three hypervariable regions, also called complementarity determining regions (CDR's) (see, Sequences of Proteins of Immunological Interest, E. Kabat et al., U.S. Department of Health and Human Services, 1983). As noted above, the CDRs are primarily responsible for binding to an epitope of an antigen. An immune complex is an antibody, such as a monoclonal antibody, chimeric antibody, humanized antibody or human antibody, or functional antibody fragment, specifically bound to the antigen. According to the present invention, the myostatin binding and/or inhibiting or suppressing antibody is preferably a short polypeptide, e.g., an Fv, Fab, and (Fab')$_2$.

Chimeric antibodies are antibodies whose light and heavy chain genes have been constructed, typically by genetic engineering, from immunoglobulin variable and constant region genes belonging to different species.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Exemplary conservative substitutions are those such as gly, ala; val, ile, leu; asp, glu; asn, gln; ser, thr; lys, arg; and phe, tyr. Humanized immunoglobulins can be constructed by means of genetic engineering (e.g., see U.S. Pat. No. 5,585,089). A human antibody is an antibody wherein the light and heavy chain genes are of human origin. Human antibodies can be generated using methods known in the art. Human antibodies can be produced by immortalizing a human B cell secreting the antibody of interest. Immortalization can be accomplished, for example, by EBV infection or by fusing a human B cell with a myeloma or hybridoma cell to produce a trioma cell. Human antibodies can also be produced by phage display methods (see, e.g., Dower et al., PCT Publication No. WO91/17271; McCafferty et al., PCT Publication No. WO92/001047; and Winter, PCT Publication No. WO92/20791), or selected from a human combinatorial monoclonal antibody library (see the Morphosys website). Human antibodies can also be prepared by using transgenic animals carrying a human immunoglobulin gene (for example, see Lonberg et al., PCT Publication No. WO93/12227; and Kucherlapati, PCT Publication No. WO91/10741).

Thus, the antibody may have the formats known in the art. Examples are human antibodies, monoclonal antibodies, humanized antibodies, chimeric antibodies, CDR-grafted antibodies.

In a preferred embodiment antibodies according to the present invention are recombinantly produced antibodies as, e.g., IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g. via dimerization of dHLXdomains,e.g. Fab-dHLX-FSx2; F(ab')2-fragments, scFv-fragments, multimerized multivalent or/and multispecificscFv-fragments, bivalent and/or bispecificdiabodies, BITE® (bispecific T-cell engager), trifunctional antibodies, polyvalent antibodies, e.g. from a different class than G; single-domain antibodies, e.g.nanobodies derived from camelid or fish immunoglobulines and numerous others.

In addition to antibodies other biopolymer scaffolds are well known in the art to complex a target molecule and have been used for the generation of highly target specific biopolymers. Examples are aptamers, spiegelmers, anticalins and conotoxins.

In a preferred embodiment the antibody format is selected from the group comprising Fv fragment, scFv fragment, Fab fragment, scFab fragment, (Fab)2 fragment and scFv-Fc Fusion protein. In another preferred embodiment the antibody format is selected from the group comprising scFab fragment, Fab fragment, scFv fragment. One of the most preferred formats is the scFab format. Naturally, these antibody fragments are linked to an anchor domain as disclosed throughout the application. In one embodiment, said anchor domain is a D domain, preferably an isolated D domain, of IGF-I as depicted in SEQ ID NO:1, a derivative thereof having at least 50% identity with SEQ ID NO: 1, or a fragment comprising at least the four C-terminal acid residues of SEQ ID NO:1, wherein said anchor domain is capable of binding to an extracellular matrix or a synthetic extracellular matrix component. In one embodiment, said anchor domain does not comprise the growth factor activity of IGF-I. In one embodiment, the binding of a synthetic compound to an extracellular matrix or a synthetic extracellular matrix component mediated by transglutaminase has fast kinetics. In one embodiment, said anchor domain preferably is a D domain of IGF-I as depicted in SEQ ID NO:1 or a fragment comprising at least the four C-terminal acid residues of SEQ ID NO:1.

Non-Ig scaffolds may be protein scaffolds and may be used as antibody mimics as they are capable to bind to ligands or antigens. Non-Ig scaffolds may be selected from the group comprising tetranectin-based non-Ig scaffolds (e.g., described in US 2010/0028995), fibronectin scaffolds (e.g. described in EP 1266025; lipocalin-based scaffolds (e.g. described in WO 2011/154420); ubiquitin scaffolds (e.g., described in WO 2011/073214), transferring scaffolds (e.g. described in US 2004/0023334), protein A scaffolds (e.g., described in EP 2231860), ankyrin repeat based scaffolds (e.g., disclosed in WO 2010/060748), microproteins, preferably microproteins forming a cystine knot) scaffolds (e.g. described in EP 2314308), Fyn SH3 domain based scaffolds (e.g. described in WO 2011/023685) EGFR-A-domain based scaffolds (e.g. described in WO 2005/040229) and Kunitz domain based scaffolds (e.g. described in EP 1941867).

In other embodiments of the above embodiments, the synthetic compound according to the preceding embodiments, wherein the second domain comprises an amino acid sequence as defined in SEQ ID NO: 12 (VATQGQC-TRWPWMCPPQGWG), or a functional variant, fragment or derivative thereof. Some of the functional variants are disclosed in WO2004058988 A2. For experiments with extracellular matrix, a cleavable linker sequence (GPQ-GIAGQ; SEQ ID No. 13) may be linked to SEQ ID NO: 1 or functional derivatives via short PEG(3)- or PEG(6)-Spacer.

In other embodiments of the above embodiments, the synthetic compound according to the preceding embodiments comprises a cleavable linker between the anchor domain and the at least one second domain, and optionally between any additional domain as defined supra.

In other embodiments a pharmaceutical composition or formulation comprising a synthetic compound as defined in any of the preceding embodiments is provided.

In other embodiments the pharmaceutical composition or formulation according to any of the preceding embodiments is suitable for localized administration.

In other embodiments the synthetic compound as defined in any of the preceding embodiments is provided for use in tissue repair in its broadest sense comprising the treatment and/or prevention (e.g., prevention from worsening/aggravation/deterioration/delaying the healing/development of chronicity of wounds) of a pathological condition (a disease, disorder, symptom of a disease, etc.) selected from the group comprising:

treatment and/or prevention of lesions, wounds, burns,
excessive scar formation, e.g., post-operative scarring, fibrosis,
in tissue regeneration in lesioned locations, e.g., of injured or wounded and/or surgically treated tendons and/or ligaments, after cosmetic surgical treatments, etc.,
prevention of inflammation in lesions,
impaired wound healing,
complications of wound healing due to bacterial infections, due to age, due to diabetes, due to cardiovascular disorders, due to sensory neuropathies, due to autoimmune diseases.

In other embodiments the synthetic compound as defined in any of the preceding embodiments or a pharmaceutical composition or formulation according to any of the preceding embodiments is provided for use in the treatment and/or prevention of a pathological condition as defined in the preceding embodiment, wherein said compound is for use in combination with an enzyme or fragment having transglutaminase activity, preferably a mammalian transglutaminase selected from the group consisting of FXIII, TG1, TG2, TG3, TG4, TG5, TG6 and TG7, more preferably human Factor XIIIa.

Subject matter of the present invention is also the co-delivery of the herein described compounds or compositions together with FXIII and fibrinogen to achieve gel formation in situ so that therapeutic moieties referred to herein may be bound or immobilized to or onto such gel.

Subject matter of the present invention is also a synthetic compound as defined in any of the preceding embodiments or the pharmaceutical composition or formulation according to any of the above embodiments for use in the treatment of lesions and/or tissue regeneration in lesioned locations and/or prevention of inflammation in lesions, bone fractures, tendinitis, heart disease, atherosclerosis and impaired wound healing, amongst other pathological states, or any of the above defined situations, diseases, conditions, or disorders in which tissue repair would be desirable, wherein said composition or formulation is suitable for the localized administration, wherein the localized administration is preferably selected from the group comprising topical administration, administration to the site of a lesion, administration to the site of surgery, wherein, in addition to the synthetic compound of the invention as defined above, a transglutaminase is either separately or simultaneously administered. Therefore, a transglutaminase as described herein may be a component of the pharmaceutical or diagnostic composition or formulations of the invention or it may be administered as component of a separate formulation or composition.

In other embodiments the synthetic compound as defined in any of the preceding embodiments or a pharmaceutical composition or formulation according to any of the preceding embodiments is provided for use in the treatment and/or prevention of a pathological condition as defined in the preceding embodiments, wherein said synthetic compound or pharmaceutical or diagnostic composition or formulation is suitable for the localized administration, wherein the localized administration is preferably selected from the group of topical administration, including transdermal, ophthalmic, nasal, otologic, enteral, pulmonal and urogenital administration or local or systemic injection, including subcutaneous, intra-articular, intravenous, intracardiac, intramuscular, intraosseous or intraperitoneal administration. In one embodiment, a synthetic compound, a pharmaceutical composition, a device, or an artificial tissue of the present invention are preferably administered locally and not systemically. In one embodiment, the terms "locally" and "localized" are used interchangeably. In one embodiment, a synthetic compound of the present invention is locally and covalently bound to an extracellular matrix or a synthetic extracellular matrix component by transglutaminase. In one embodiment, said local administration results in localized anchorage of a synthetic compound of the present invention comprising a myostatin inhibitor, and said localized anchorage allows for prolonged local inhibitory activity of said myostatin inhibitor compared to a systemic administration of said myostatin inhibitor.

In other embodiments a device comprising a synthetic compound or pharmaceutical composition or a pharmaceutical or formulation as defined in any of the preceding embodiments is provided.

In other embodiments the device according to the preceding embodiment is provided, wherein the device is suitable as a delivery system for immediate and/or sustained release of a compound as defined in any one of the preceding embodiments.

In other embodiments the device according to the preceding embodiment is provided, wherein said device is selected from the group comprising patches, implants, scaffolds, porous vascular grafts, stents, and/or wound dressings composed of a biocompatible fleece, preferably made of hydrocolloids, polyacrylate, alginate, hydrogels, or foams, and/or artificially produced tissues, bone-replacements, polymer networks, hydrogels, preferably composed of fibrin, collagen, elastin, hyaluronic acid or silk proteins.

In other embodiments an in vitro method of tissue engineering is provided comprising the steps:

providing an extracellular matrix substrate comprising a specific amino acid sequence serving as a target for transglutaminase, providing a synthetic compound as defined in any of the preceding claims, exposing the extracellular matrix substrate and the compound as defined in steps (i) and (ii) to an enzyme having transglutaminase activity under conditions and in a medium suitable for transamidation.

In other embodiments an artificial tissue obtainable by a method according to the preceding embodiment is provided.

In one embodiment, a method of the present invention allows for in situ anchorage, preferably by covalent linkage, of a synthetic compound of the present invention to an extracellular matrix or to a synthetic extracellular matrix component.

In other embodiments the artificial tissue according to the preceding embodiment is provided for use in the treatment and/or prevention of a pathological condition (a disease, disorder, symptom of a disease, etc.) selected from the group comprising:

treatment and/or prevention of lesions, wounds, burns, excessive scar formation, e.g., post-operative scarring, fibrosis, in tissue regeneration in lesioned locations, e.g., of injured or wounded and/or surgically treated tendons and/or ligaments, after cosmetic surgical treatments, etc., prevention of inflammation in lesions, impaired wound healing, complications of wound healing due to bacterial infections, due to age, due to diabetes, due to cardiovascular disorders, due to sensory neuropathies, due to autoimmune diseases.

As used herein, the term "extracellular matrix component" comprises, e.g., fibronectin, osteopontin, decorin, collagen, hyaluronic acid, elastin, as well as mixtures thereof, e.g., in form of matrices, gels, networks, freeze-dried or otherwise bound components, such as fibronectin that is attached to a support, etc. In one embodiment, an extracellular matrix component and/or extracellular matrix substrate preferably comprises fibronectin.

In embodiments of the invention, the derivatives and/or fragments maintain the lysine residue at position 6 of SEQ ID NO: 1. Some embodiments of such derivatives and/or fragments are depicted in the Sequence Listing in SEQ ID Nos: 2 to 10.

In context of the present application, directly linked or indirectly linked refers to peptidic linkages or peptide bonds, covalently binding, etc. Suitable conjugation or linking methods include covalent or non-covalent (such as biotin-(strept)avidin systems or heparin binding domains), preferably site-specific bioconjugation strategies. The coupling can be performed by chemical or enzymatic bio-orthogonal approaches. In one embodiment, said directly or indirectly linked preferably relates to a covalent binding.

Subject matter of the present invention is also a synthetic compound according to any one of the preceding embodiments, wherein further domains, apart from the second domain as defined above (e.g., a myostatin inhibiting or binding or antagonizing molecule), comprise or consist of therapeutic agents selected from the group comprising a growth factor (e.g. IGF-1, FGF2, VEGF, bone morphogenetic protein(s), e.g., BMP-2), a therapeutically active polypeptide, anti-apoptotic molecules, anti-inflammatory molecules, antibiotics, hormones, antibodies, immune modulating cytokines (Interleukins, e.g. IL-2, IL-4; Interferons, e.g. INFα2a).

In the context of the present invention, the term "therapeutic treatment", relates to the amelioration of the respective underlying disease or symptom and comprises the alleviation of such disease or symptom, the reduction of undesirable disease symptoms, the improvement of health, the prevention from worsening or the occurrence of a disease or symptom in a patient in need thereof being subjected to the treatment.

Subject matter of the present invention is also a synthetic compound according to any one of the preceding embodiments, comprising a detectable moiety selected from the group comprising fluorescent moieties, or another detectable moiety, e.g. a chromogenic compound, a radioactive compound, etc. Fluorescent moieties and other detectable moieties can be selected from those known to a person skilled in the art, e.g., those available on the market from companies such as Thermo Fisher, Sigma Aldrich, etc.

Subject matter of the present invention is also a synthetic compound according to any one of the preceding embodiments, further comprising a cleavable linker. The cleavable linker may be selected from those responding to elevated protease concentrations during disease onset or progression (e.g., matrix metalloproteases, in case of inflammatory conditions) or to changes in external stimuli, such as reduction in pH or elevated H2O2 concentrations.

Subject matter of the present invention is therefore also a synthetic compound according to any one of the preceding embodiments, wherein said compound further comprises a cleavable linker between the anchor domain and the therapeutic molecule or detectable moiety. The cleavable linker may be derived from collagen type I, or may be any linker molecule that can be cleaved in a desired environment of use or administration of the herein described products (synthetic compounds, pharmaceutical or diagnostic compositions/formulations, devices as defined herein). In embodiments according to any of the preceding embodiments, the cleavable linker(s) may be derived from collagen type I, may have the SEQ ID NO: 13 or be a functional derivative thereof that is cleavable.

Subject matter of the present invention is also a device comprising a synthetic compound or pharmaceutical composition or a pharmaceutical formulation as defined in any of the preceding embodiments. The device can incorporate any of the compounds as defined in the preceding embodiments, together with a transglutaminase to provide sustained release of the compounds and the crosslinking enzyme.

Subject matter of the present invention is also a device according to the previous embodiments, wherein the device is suitable as a delivery system for immediate and/or sustained release of a compound as defined in any one of the preceding embodiments. The devices according to the present invention may therefore also be used as drug delivery systems or controlled drug release systems. In one embodiment, a drug delivery system of the present invention comprises a myostatin inhibitor coupled to an anchor domain.

Subject matter of the present invention is also a device according to the preceding embodiments, wherein said device is selected from the group comprising patches, artificially produced tissues, implants, scaffolds, porous vascular grafts, stents, wound dressings composed of a biocompatible fleece (preferably made of hydrocolloids, polyacrylate, alginate, hydrogels, or foams), artificially produced tissues, bone-replacements, polymer networks, hydrogels (preferably composed of fibrin, collagen, elastin, hyaluronic acid or silk proteins).

Subject matter of the present invention is also an in vitro method of tissue engineering comprising the steps of:

providing an extracellular matrix substrate comprising a specific amino acid sequence serving as a target for a transglutaminase, preferably FXIIIa providing a synthetic compound as defined in any of the preceding claims, exposing the extracellular matrix substrate and the compound as defined in steps (i) and (ii) to an enzyme having transglutaminase activity under conditions and in a medium suitable for transamination.

The extracellular matrix substrate is preferably a target for human FXIIIa and may be fibronectin or a suitable derivative or fragment thereof that maintains its activity of serving as a target for the immobilization of the synthetic compounds as defined herein. The target may be modified with a glutamine substrate, such as NQEQVSPL (SEQ ID NO: 11).

Subject matter of the present invention is also an artificial tissue obtainable by a method according to the preceding embodiment.

In one embodiment, said artificial tissue comprises a synthetic compound of the present invention covalently coupled to an extracellular matrix substrate. A person skilled in the art understands how said extracellular matrix substrate can be selected and/or prepared to comprise desired properties, such as with regard to the cross-linking level, texture, mechanical properties, and/or cell interaction.

Subject matter of the present invention is also an artificial tissue according to the preceding embodiment for use in the treatment of lesions, wounds, diseases or conditions requiring tissue replacements selected from the group comprising injuries in general, surgically treated tissues, tendinitis, rheumatoid arthritis, osteoarthritis, bone replacements, tooth replacements, diabetic ulcers, post-surgical lesions, etc.

Subject matter of the present invention is also a method of incorporating exogenous peptides into hydrogels (preferably composed of fibrin, collagen, elastin, hyaluronic acid or silk proteins) using the herein described synthetic compounds.

Subject matter of the present application is a synthetic compound as defined in the preceding embodiments for use in the treatment of lesions and/or tissue regeneration and/or prevention of inflammation, wherein said compound comprises at least one anchoring domain that is selected from the group comprising:

i) the D domain of Insulin Growth Factor-1 (IGF-I) as depicted in SEQ ID NO: 1, ii) a derivative of i) having at least 50% identity with SEQ ID NO: 1, wherein the derivative maintains the capability of acting as a substrate for transglutaminases, e.g., (human) FXIIIa, and can be immobilized on a suitable substrate or matrix and preferably consists of the four C-terminal amino acids of SEQ ID NO: 1 (AKSA); the derivative preferably has at least 60% identity with SEQ ID NO: 1, or at least 70% identity with SEQ ID NO: 1, or at least 75% identity with SEQ ID NO: 1, or at least 80% identity with SEQ ID NO: 1, or at least 85% identity with SEQ ID NO: 1, or at least 90% identity with SEQ ID NO: 1, or at least 95% identity with SEQ ID NO: 1;

iii) a fragment of i) or ii), wherein said fragment comprises at least the four C-terminal amino acid residues depicted in SEQ ID NO: 1, or a fragment comprising the at least five, or a fragment comprising the at least six, or a fragment comprising the at least seven amino acids of SEQ ID NO: 1, or a derivate thereof having at least 75% identity, at least 80% identity, or at least 85% to the amino acid sequence depicted in SEQ ID NO: 1, wherein said fragments comprise at least the four C-terminal amino acid residues depicted in SEQ ID NO: 1.

As used herein said fragment as part of the synthetic compound described herein may be incorporated in medicaments, compositions (liquid formulations suitable for injection into diseased tissue, solid formulations including lyophilized or spray-dried formulations for reconstitution before parenteral administration, patches, gels, salves, ointments, endoscopically administrable compositions for local or system release, e.g. stents, artificial bones (bone replacements), skin, etc.), or devices that are used for any functional activities underlying the purposes indicated herein, in particular in the treatment of lesions, or in vitro into compositions or media used for tissue engineering purposes.

The synthetic compound may be a chimeric (fusion) polypeptide comprising any of the above synthetic compounds i) to iii) and at least one (cleavable) linker peptide and at least one further therapeutically or preventively active domain, e.g., another polypeptide sequence.

As used herein, a "chimeric polypeptide" or a "fusion polypeptide" designates any polypeptide that comprises the D domain of IGF as defined above or a derivative or fragment thereof that maintains the capacity of being recognized and immobilized on or incorporated into a suitable substrate or matrix using a transglutaminase (e.g., FXIIIa, preferably human FXIIIa), wherein said polypeptide is chemically bound (e.g., with a peptide bond) or otherwise linked to a second domain (preferably a polypeptide sequence encoding a myostatin inhibiting, binding, suppressing and/or antagonizing molecule, which means that it is not bound to the adjacent polypeptide found in natural (e.g., wild-type) IGF-I molecules neighboring the D domain of said protein; the second domain may be derived from any polypeptide of interest, e.g., growth factors, hormones, therapeutically active peptides, particularly peptides involved in the regeneration, repair and growth of tissues or cells, but the heterologous peptides may also be artificial sequences that have a desired function, e.g., acting as a spacer or a binding site for an antibody or for any other molecule of interest, for example, a linker molecule that can be cleaved to release a polypeptide or other molecule having a desired function, e.g., being involved in the regeneration, repair and growth of tissues or cells. In one embodiment, a synthetic compound of the present invention comprises a linker between the anchor domain and the at least one second domain, wherein said linker allows for release of said second domain in situ by enzymatic cleavage. In one embodiment, said anchor domain is a fragment of IGF-I which is a minimal fragment of IGF-I sufficient to mediate a binding to the extracellular matrix or to an extracellular matrix component, and which does not alter the therapeutic and/or preventive activity of the second domain, preferably said myostatin inhibitor, coupled thereto.

Subject-matter of the invention is also a synthetic compound for use in tissue repair in its widest sense, e.g., the treatment of lesions and/or tissue regeneration according to the above embodiments, wherein the treatment of lesions and/or tissue regeneration is for post-surgical lesions, skin lesions, tendon lesions complications, and arthritic lesions, wounds or injuries of any type, particularly wounds that are associated with various diseases or conditions such as ageing, diabetes, sensory neuropathies, genetic diseases (e.g., epidermolysis bullosa) autoimmune-inflammatory diseases (e.g., sporadic inclusion body myositis, sIBM) cachexia (e.g., tumor-induced cachexia), muscle wasting diseases, HIV infections, neoplasias, cardiac diseases, such as heart failure, pulmonary diseases, sarcopenia, artificial ventilation, etc. as discussed above.

As used herein, "lesion complications" refers to a condition, wherein the healing process is not progressing as intended or is reversed, or wherein an infection or inflammation or any undesirable immune reaction occurs, e.g. accompanied by non-intended apoptosis or necrosis, fever, and so forth.

The synthetic compound may be any of the above specified synthetic compounds, in particular those having the desired functional activity, which includes pharmaceutically or therapeutically or diagnostically effective or active polypeptides or other molecules for therapeutic use or detectable moieties as defined above. The synthetic compounds use for such treatments are used at therapeutically or preventive effective doses/amounts.

Subject-matter of the invention is also a synthetic compound product as defined in any of the foregoing embodiments, particularly, in the above embodiments relating to the synthetic compounds for use in tissue repair comprising the treatment of lesions and/or tissue regeneration and/or prevention of inflammation and/or prevention of worsening of physiological processes that are associated with tissue repair, e.g., exceeding scar formation.

Subject-matter of the invention is also a pharmaceutical composition/formulation as defined in any of the foregoing embodiments, further comprising an enzyme having transglutaminase activity. In some embodiments, the enzyme may be an activated transglutaminase, such as Factor XIIIa (preferably human FXIIIa) or tissue transglutaminase, or the enzyme may be an inactive transglutaminase that is activated upon administration by thrombin. As FXIIIa requires the presence of calcium as cofactor, exogenous calcium sources may also be included into the inventive compositions or formulations, e.g., CaCl2.

Subject-matter of the invention is also a device comprising a pharmaceutical composition or a pharmaceutical formulation as defined in any of the foregoing embodiments. A device may take any form that is suitable to deliver the synthetic compounds or any one of the compositions or formulations of the present invention. It may comprise biological and/or synthetic materials and may take form of a patch, a stent, an implantable device, an artificially produced tissue (which may be obtainable by means of tissue engineering), an artificial bone or ankle, soluble components of ECM or synthetic biomaterials, hydrogels or components able to be cross-linked in situ catalyzed by transglutaminase (e.g. fibrin) etc.

Subject-matter of the invention is also a device as defined in any of the foregoing embodiments, wherein the device is a delivery system for immediate and/or sustained release of the synthetic compound as defined in any of the foregoing embodiments.

Subject-matter of the invention is also a method of treatment of an individual in need thereof and/or the amelioration of and/or the prevention of deterioration of a disease in an individual in need thereof, e.g., in a patient having a lesion or wound or catabolic/atrophic condition as defined in any one of the preceding embodiments, by administration to said individual of a therapeutically efficient amount of any of the synthetic compounds and/or pharmaceutical compositions as defined above.

The administration of the compounds according to this invention and pharmaceutical compositions according to the invention may be performed in any of the generally accepted modes of administration available in the art. Illustrative examples of suitable modes of administration include intravenous, oral, nasal, inhalable, parenteral, topical, transdermal and rectal delivery. Parenteral and intravenous delivery forms are preferred. In aspects of the invention injectable compositions comprising a therapeutically effective amount of the compounds of the invention are provided, including salts, esters, isomers, solvates, hydrates and polymorphs thereof, at least one vehicle comprising water, aqueous solvents, organic solvents, hydro-alcoholic solvents, oily substances, or mixtures thereof, and optionally one or more pharmaceutically acceptable excipients. Standard knowledge regarding these pharmaceutical ingredients and pharmaceutical formulations/compositions may be found, inter alia, in the 'Handbook of Pharmaceutical Excipients'; Edited by Raymond C Rowe, Paul J Sheskey, Walter G Cook and Marian E Fenton; May 2012 and/or in Remington: The Science and Practice of Pharmacy, 19th edition. The pharmaceutical compositions may be formulated in the form of a dosage form for oral, intravenous, nasal, inhalable, parenteral, topical, transdermal and rectal and may thus comprise further pharmaceutically acceptable excipients, such as buffers, solvents, preservatives, disintegrants, stabilizers, carriers, diluents, fillers, binders, lubricants, glidants, colorants, pigments, taste masking agents, sweeteners, flavorants, plasticizers, and any acceptable auxiliary substances such as absorption enhancers, penetration enhancers, surfactants, co-surfactants, and specialized oils.

The proper excipient(s) is (are) selected based in part on the dosage form, the intended mode of administration, the intended release rate, and manufacturing reliability. Examples of common types of excipients include also various polymers, waxes, calcium phosphates, sugars, etc.

Polymers include cellulose and cellulose derivatives such as HPMC, hydroxypropyl cellulose, hydroxyethyl cellulose, microcrystalline cellulose, carboxymethylcellulose, sodium carboxymethylcellulose, calcium carboxymethylcellulose, and ethylcellulose; polyvinylpyrrolidones; polyethylenoxides; polyalkylene glycols such as polyethylene glycol and polypropylene glycol; and polyacrylic acids including their copolymers and crosslinked polymers thereof, e.g., Eudragit° (Rohm), polycarbophil, and chitosan polymers. Waxes include white beeswax, microcrystalline wax, carnauba wax, hydrogenated castor oil, glyceryl behenate, glycerylpalmitol stearate, and saturated polyglycolyzed glycerate. Calcium phosphates include dibasic calcium phosphate, anhydrous dibasic calcium phosphate, and tribasic calcium phosphate. Sugars include simple sugars, such as lactose, maltose, mannitol, fructose, sorbitol, saccharose, xylitol, isomaltose, and glucose, as well as complex sugars (polysaccharides), such as maltodextrin, amylodextrin, starches, and modified starches.

The pharmaceutical compositions of the present invention may be formulated into various types of dosage forms, for instance as solutions or suspensions, or as tablets, capsules, granules, pellets or sachets for oral administration. A particularly preferred pharmaceutical composition is in the form of a solid oral dosage form, preferably tablets. The tablet is preferably a tablet for swallowing. It may optionally be coated with a film coat comprising, in essence, any suitable inert coating material known in the art. The above lists of excipients and forms are not exhaustive.

The pharmaceutical composition of the present invention can be manufactured according to standard methods known in the art. Granulates according to the invention can be obtained by dry compaction or wet granulation. These granulates can subsequently be mixed with e.g. suitable disintegrating agents, glidants and lubricants and the mixture can be compressed into tablets or filled into sachets or capsules of suitable size. Tablets can also be obtained by direct compression of a suitable powder mixture, i.e. without any preceding granulation of the excipients. Suitable powder or granulate mixtures according to the invention are also obtainable by spray drying, lyophilization, melt extrusion, pellet layering, coating of the active pharmaceutical ingredient or any other suitable method. The so obtained powders or granulates can be mixed with one or more suitable ingredients and the resulting mixtures can be delivered in sterile primary packaging devices for reconstitution before parenteral administration Injectable compositions of the present invention may contain a buffer (for example, sodium dihydrogen phosphate, disodium hydrogen phosphate and the like), an isotonizing agent (for example, glucose, sodium chloride and the like), a stabilizer (for example, sodium hydrogen sulfite and the like), a soothing agent (for example, glucose, benzyl alcohol, mepivacaine hydrochloride, xylocaine hydrochloride, procaine hydrochloride, carbocaine hydrochloride and the like), a preservative (for example, p-oxybenzoic acid ester such as methyl p-oxybenzoate and the like, thimerosal, chlorobutanol, benzyl alcohol and the like) and the like, if necessary. In addition, the injectable composition of the present invention may contain vitamins and the like. Further, injectable compositions of the present invention may contain an aqueous solvent, if necessary. Examples of the aqueous solvent include purified water for injection, physiological saline solution, and glucose solution. In injectable compositions of the present invention, the pharmaceutical compound may be solid. As used herein, the "solid" comprises crystals and amorphous substances which have conventional meanings. The form of the solid component is not particularly limited, but powder is preferred in view of dissolution rate.

Pharmaceutical Compositions

Still another aspect of the present invention relates to the use of the synthetic compound according to the above embodiments and appending claims as an active ingredient, together with at least one pharmaceutically acceptable carrier, excipient and/or diluents for the manufacture of a pharmaceutical composition for tissue repair, particularly the treatment and/or prevention of worsening of lesions or wounds as defined herein.

Such pharmaceutical compositions comprise the peptide as an ECM anchor, together with an active ingredient and at least one pharmaceutically acceptable buffer, carrier, excipient, diluents, preservatives or the like. The pharmaceutical compositions of the present invention can be prepared in a conventional solid or liquid carrier or diluents and a conventional pharmaceutically-made adjuvant at suitable dosage level in a known way. Preferably the compound is suitable for local administration or suitable for topical administration.

Administration forms include, for example, pills, tablets, film tablets, coated tablets, capsules, liposomal formulations, micro- and nano-formulations, powders and deposits. Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain the compounds according to the present invention.

In some embodiments of the invention, local, e.g. topical, administration methods of the compounds and/or compositions disclosed herein are preferred.

The compounds of the invention can also be administered in form of its pharmaceutically active salts. Suitable pharmaceutically active salts comprise acid addition salts and alkali or earth alkali salts. For instance, sodium, potassium, lithium, magnesium or calcium salts can be obtained.

The pharmaceutical compositions according to the present invention will typically be administered together with suitable carrier materials selected with respect to the intended form of administration, i.e. for oral administration in the form of tablets, capsules (either solid filled, semi-solid filled or liquid filled), powders for constitution, aerosol preparations consistent with conventional pharmaceutical practices. Other suitable formulations are hydrogels, elixirs, dispersible granules, syrups, suspensions, creams, lotions, solutions, emulsions, suspensions, dispersions, and the like. Suitable dosage forms for sustained release include tablets having layers of varying disintegration rates or controlled release polymeric matrices delivered with the active components. The pharmaceutical compositions may be comprised of 1 to 95% by weight of the compounds of the invention.

As pharmaceutically acceptable carrier, excipient and/or diluents can be used HSA, lactose, sucrose, cellulose, and/or mannitol.

Suitable binders include starch, gelatin, natural sugars, corn sweeteners, natural and synthetic gums such as acacia, sodium alginate, carboxymethyl-cellulose, polyethylene glycol and waxes. Among the lubricants that may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below. Additionally, the compositions of the present invention may be formulated in sustained release form to provide the rate controlled release of any one or more of the components or active ingredients to optimize the therapeutic effects. Suitable dosage forms for sustained release include controlled release polymeric matrices or hydrogels embedding the active components. Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for parenteral administration. Such liquid forms include solutions, suspensions and emulsions.

The compounds of the present invention may also be deliverable transdermally. The transdermal compositions may take the form of creams, lotions, aerosols and/or emulsions and can be included in a transdermal patch of the matrix or reservoir type as are conventional in the art for this purpose.

The transdermal formulation of the compounds of the invention is understood to increase the bioavailability of said compound into the circulating blood. One problem in the administration of peptidic therapeutics in general is the loss of bioactivity due to the formation of insolubles in aqueous environments or due to degradation. Therefore, stabilization of compounds for maintaining their fluidity and maintaining their biological activity upon administration to the patients in need thereof needs to be achieved. Prior efforts to provide active agents for medication include incorporating the medication in a polymeric matrix whereby the active ingredient is released into the systemic circulation. Known sustained-release delivery means of active agents are disclosed, for example, in U.S. Pat. Nos. 4,235,988, 4,188,373, 4,100,271, 447,471, 4,474,752, 4,474,753, or 4,478,822 relating to polymeric pharmaceutical vehicles for delivery of pharmaceutically active chemical materials to mucous membranes. The pharmaceutical carriers are aqueous solutions of certain polyoxyethylene-polyoxypropylene condensates. These polymeric pharmaceutical vehicles are described as providing for increased drug absorption by the mucous membrane and prolonged drug action by a factor of two or more. The substituents are block copolymers of polyoxypropylene and polyoxyethylene used for stabilization of drugs such as insulin.

Aqueous solutions of polyoxyethylene-polyoxypropylene block copolymers (poloxamers) are useful as stabilizers for the compounds. Aside from serving as a stabilizer for the compound, poloxamers provide excellent vehicles for the delivery of the compound, and they are physiologically acceptable. Poloxamers, also known by the trade name Pluronics (e.g. Pluronic F127, Pluronic P85, Pluronic F68) have surfactant properties that make them useful in industrial applications. Among other things, they can be used to increase the water solubility of hydrophobic, oily substances or otherwise increase the miscibility of two substances with different hydrophobicities. For this reason, these polymers are commonly used in industrial applications, cosmetics, and pharmaceuticals. They have also been used as model systems for drug delivery applications. In situ gelation of pharmaceutical compositions based on poloxamer that are biologically triggered are known in the art (e.g. U.S. Pat. No. 5,256,396), describing compositions containing poloxamer 407 and water at specified concentrations.

Gels refer to the active ingredients dispersed or solubilized in a hydrophilic semi-solid matrix. Powders for constitution refer to powder blends containing the active ingredients and suitable diluents which can be suspended in water and may contain optionally buffer salts, lactose, amino acids, excipients, sugars and isotonisation reagents.

Recently, increasingly improved and potent protein-based and peptide-based drugs have been developed by the biotech industry. However, the preventive/prophylactic and/or therapeutic use of many other protein- or peptide-based compounds has been hampered because of their susceptibility to proteolytic breakdown, rapid plasma clearance, peculiar dose-response curves, immunogenicity, bioincompatibility, and/or the tendency of peptides and proteins to undergo aggregation, adsorption, and/or denaturation. These characteristics often render traditional methods of drug delivery ineffective or sub-optimal when applied to protein or peptide based drugs. Therefore, an immense amount of interest has been increasingly placed on controlled and/or sustained release drug delivery systems to maintain the therapeutic efficacy or diagnostic value of these important classes of biologically active agents. One of the primary goals of sustained delivery systems is to maintain the levels of an active agent within an effective range and ideally at a constant level. One approach for sustained delivery of an active agent is by microencapsulation, in which the active agent is enclosed within a polymeric matrix. The importance of biocompatible and/or biodegradable polymers as carriers for parenteral drug delivery systems is now well established. Biocompatible, biodegradable, and relatively inert substances such as poly(lactide) (PLA) or poly(lactide-co-glycolide) (PLG) structures such as microparticles or films containing the active agent to be administered are commonly employed sustained delivery devices (for review, see M. Chasin, Biodegradable polymers for controlled drug delivery. In: J. O. Hollinger Editor, Biomedical Applications of Synthetic Biodegradable Polymers CRC, Boca Raton, FL (1995), pp. 1-15; T. Hayashi, Biodegradable polymers for biomedical uses. Prog. Polym. Sci. 19 4 (1994), pp. 663-700; and Harjit Tamber, Pal Johansen, Hans P. Merkle and Bruno Gander, Formulation aspects of biodegradable polymeric microspheres for antigen delivery Advanced Drug Delivery Reviews, Volume 57, Issue 3, 10 Jan. 2005, Pages 357-376). A relatively steady release of one or more active agents incorporated within such polymers is possible because of the degradation profile of these polymers in an aqueous environment. By encapsulating active agents in a polymer matrix in various forms such as microparticles and/or films the active agent is released at a relatively slow rate over a prolonged time. Achieving sustained drug release in such a manner may afford less frequent administration, thereby increasing patient compliance and reducing discomfort; protection of the therapeutic compound within the body; potentially optimized prophylactic or therapeutic responses and prolonged efficacy; and avoidance of peak-related side-effects by maintaining more-constant blood levels of the active agent. Furthermore, these compositions can oftentimes be administered by injection, allowing for localized delivery and high local concentrations of the active agents.

With regard to highly active biologics, such as growth factors, local in the form of a bolus injection results in rapid diffusion from the region of interest and can cause severe side effects and limit efficacy. The oldest way is to use biophysical retention by changing the biophysical properties in form of viscosity, porosity, hydrophobicity or charge of the material to attain a purposeful delivery. This strategy often substantially modifies the properties of the tissue and conditions for cells, requiring more appropriate, biocompatible release mechanisms. Novel methods follow a more precise and regulated path to deliver low dose of bioactive substances by using the natural ability of certain growth factors to interact with ECM glycoproteins e.g. heparin binding sites of FGF or using ECM glycoproteins or ECM fragments. The natural retention of growth factors in the ECM provides a method of controlled release, triggered by the disease itself and not external factors.

Methods of Treatment

As discussed above, the present invention provides a method of treatment of a pathological condition or disease, in particular, a method of tissue repair, treatment of and/or prevention of worsening of any type of wound lesions benefitting from the activity of myostatin inhibition. Treatment includes any of amelioration, alleviation, prevention from worsening, and curing a pathological condition or disease such as defined above, e.g., a wound or lesion of any tissue, e.g. a surgical wound, an (auto-) inflamed site of the patient's body, etc. Optionally, diseases may also be treated with further therapeutically active compounds in addition to myostatin inhibitors/binders/suppressors/antagonists.

Treatment methods of the invention comprise the step of administering to a subject a therapeutically effective amount of a synthetic compound according to the invention or a pharmaceutical composition of the invention. The administration may be effected by any route, e.g., dermally, parenterally, topically, etc.

In some embodiments, local administration methods of the synthetic compounds and/or compositions disclosed herein are preferred.

As indicated previously "therapeutically effective amount" of a synthetic compound according to the invention preferably refers to the amount necessary to achieve the therapeutic outcome.

The choice of the optimal dosage regime and duration of medication, particularly the optimal dose and manner of administration of the active compounds necessary in each case can be determined by a person skilled in the art on the basis of his/her expert knowledge.

Subject matter of the present invention is also any of the above the above synthetic compounds in method of manufacturing a medicament for the treatment of any of the above mentioned conditions or diseases.

As defined above, the pharmaceutical compositions, formulations or medicaments for administration to an individual in need thereof may, as further component, comprise a transglutaminase. Alternatively, a composition, formulation or medicament comprising a transglutaminase may be administered separately.

Tissue Engineering Methods

Subject matter of the present invention is also a method of tissue engineering using the compounds disclosed herein, wherein these compounds are substrates subjected to a transglutaminase reaction, thereby immobilizing the substrates to a material, e.g. another type of substrate, a matrix (such as naturally derived or synthetic ECM or ECM components), which may comprise biomolecules and/or synthetic molecules that act as scaffold for the immobilization. Tissue engineering scaffolds made of microporous scaffolds containing nanofibrous, nanoporous hydrogels formed from self-assembling peptides. These scaffolds provide a template on which cells can migrate, divide, secrete new matrix and differentiate. Typical tissue engineering scaffolds are porous and can be categorized as having pores on either a micrometer scale, i.e. microporous, or a nanometer scale, i.e. nanoporous. Scaffolds having pores on a micrometer scale, or having average pore diameter of about 10 to 1000 microns, are composed of a variety of biocompatible materials including metals, ceramics and polymers. Such scaffolds include solid-cast structures, open-pore foams, felts, meshes, nonwovens, woven and knitted constructs. The mechanical and conformational properties can be chosen by composition of the material and the design of the scaffold. Desirable mechanical properties include the ability to be sutured in place and good handling strength.

Composition, design and construction of the scaffold are also important to how tissue responds to the scaffold. The scaffold can be shaped to maximize surface area, to allow adequate diffusion of nutrients and growth factors to cells present in or growing into it. For example, the maximum distance over which adequate diffusion through densely packed cells can occur is in the range of about 100 to 300 microns, under conditions similar to those that occur in the body, wherein nutrients and oxygen diffuse from blood vessels moving into the surrounding tissue. Taking these parameters into consideration, one of skill in the art would configure a scaffold having pores on a micrometer scale as having sufficient surface area for the cells to be nourished by diffusion until new blood vessels interdigitate the implanted scaffold.

Scaffolds having pores on a nanometer scale, e.g. having average pore diameter of about 10 nanometers to 1 micron, are often composed of hydrogels. A hydrogel is a substance formed when a natural or synthetic organic polymer is cross-linked via covalent, ionic or hydrogen bonds to create a three-dimensional open-lattice structure, which entraps water molecules and forms a gel. Examples of materials that can be used to form a hydrogel include polyamides, methylcellulose, collagen, extracellular matrix (ECM), polysaccharides such as alginate, polyphosphazines, polyacrylates which are crosslinked tonically, high molecular weight poly (oxyalkylene ether) block copolymers such as those sold under the tradename PLURONCIS (BASF Corp., Mount Olive, N.J.), nonionic polymerized alkylene oxide compounds such as those sold under the tradename TETRON-CIS (BASF Corp., Mount Olive, N.J.), or polyethylene oxide-polypropylene glycol block copolymers which are crosslinked by temperature or pH, respectively.

Hydrogels provide conformable, malleable, or injectable materials for administering cells into a tissue. They do not, however, have mechanical integrity. Synthetic hydrogels can be sterilized and do not have the risk of associated infectious agents. However, most synthetic hydrogels do not mimic the extracellular matrix and therefore do not direct cellular growth or function. Hydrogels of natural extracellular matrix are biocompatible and can mimic the native cellular environment. However, natural hydrogels, unless made from autologous material, may elicit an immune response and may have associated infectious agents. Natural hydrogels, such as EHS mouse sarcoma basement membrane, or fibrin, have a fiber diameter of about 5 to about 10 nanometers, water content of about 80 to about 97 weight percent and average pore diameter of about 50 to about 400 nanometers.

The present invention relates to tissue-engineering scaffolds comprising a microporous scaffold comprising a biocompatible material suitable for use in tissue-engineering scaffolds and a nanofibrous, nanoporous hydrogel formed at least partially from, or supported in growth and development by the compounds of the present invention. At least a portion of the hydrogel is disposed within the pores of the microporous scaffold, thus providing tissue-engineering scaffolds having average pore diameters in the nanometer range and that provide both mechanical properties suitable for implantation into a body of a mammal and excellent tissue response once implanted in the body. The materials used to form the microporous scaffold and the nanofibrous, nanoporous hydrogel may have similar or different degradation times and may be seeded with cells or contain bioactive compounds. The bioactive synthetic compounds of the present invention can be immobilized on the scaffold or on the components of the hydrogel catalyzed by transglutaminase to provide a controlled release as a function of protease activity in contrast to the unspecific adsorption and diffusion of conventional approaches.

EXAMPLES SECTION

Example 1

Starting off by examination of the specificity and efficacy of the IGF-I D chain, the isolated sequence (PLKPAKSA) was coupled to a glutamine substrate derived from α-2 plasmin inhibitor, achieving >90% conversion within less than 10 minutes.

Consequently, this TGase tag was attached to the C-terminus of the myostatin inhibitor (MI) rendering it into substrate for transglutaminases and catalyzing the crosslinking to ECM components (FIG. 3A).

In a second set, a bioresponsive linker was integrated between the myostatin inhibitor sequence and the TGase tag. With this approach, a tailored release of MI from the ECM in case of increased requirement can be achieved. The cleavable linker responds to elevated matrix metalloproteinase concentrations during inflammation and enables bioresponsive release of the MI into the surrounding tissue in states of inflammatory flares, preventing deeper injuries to the muscle or skeletal tissue in case of complicated wounds (FIG. 3B).

Example 2

As proof of concept, the MI with TG tag ("MI-D chain") was immobilized onto cell derived, isolated extracellular matrix (ECM). The ECM was produced by NIH3T3 fibroblasts and on day 6 decellularized and washed to remove cell debris and adsorbed proteins. Taking advantage of the intrinsic property of fibronectin, representing a glutamine donor for blood coagulation factor XIII, the MI-D chains were immobilized on the N-terminus of fibronectin without impairment of its capacity to bind and inhibit myostatin (FIG. 4).

According to previous studies, FXIIIa shows specificity for glutamine residue #3 of fibronectin and this Q3 represents the main target for conjugations [13]. Labelling of fibronectin at the N-terminus was found to not preclude cellular recognition of Fn conjugates or abolish Fn-Fn interactions that are essential for fibril formation [14]. MI-D chains were immobilized on ECM with high efficacy (FIG. 4A) and the co-localization with fibronectin confirmed using confocal laser scanning microscopy (FIG. 4B). Bioactivity of immobilized MI was confirmed by capturing myostatin using ELISA and consequently the restoration of mouse myoblast cells to differentiate in presence of myostatin (FIG. 4C, D).

In a second set, a protease-cleavable linker (PCL) was integrated between the MI and the TG recognition sequence responding to locally upregulated matrix metalloproteinases (MMPs) in inflamed tissue (FIG. 5). If a flaring inflammation in the wounded tissue occurs, accompanied by invasion of macrophages and release of MMPs, the inter-positioned PCL is cleaved, releasing the MI and instantly inhibiting the flaring inflammation and preventing apoptosis of surrounding cartilage and muscle cells. The integration of the PCL enabled a faster MI release when exposed to MMPs ("MI1") in comparison to the directly-bound MI ("MI2") (FIG. 5A) and released MI was bioactive in terms of myostatin inhibition (FIG. 5B).

The co-delivery using transglutaminase as a physiological strategy does not entail any immunogenic potential, as it involves an endogenous protease for immobilization on a biological matrix under physiological conditions, thereby imitating a completely natural process. This promising strategy may therefore be transferred into clinical application for tissue repair, e.g., prevention of wound complications, especially in light of the high prevalence of chronic wounds and ulcers of diabetic patients.

In the injured tissue, transglutaminase catalyzes the cross-linking of the MI with endogenous fibronectin on the ECM, resulting in local accumulation of the MI, thereby neutralizing upregulated myostatin at the wound site (FIG. 6).

DESCRIPTION OF FIGURES

Figure 6:
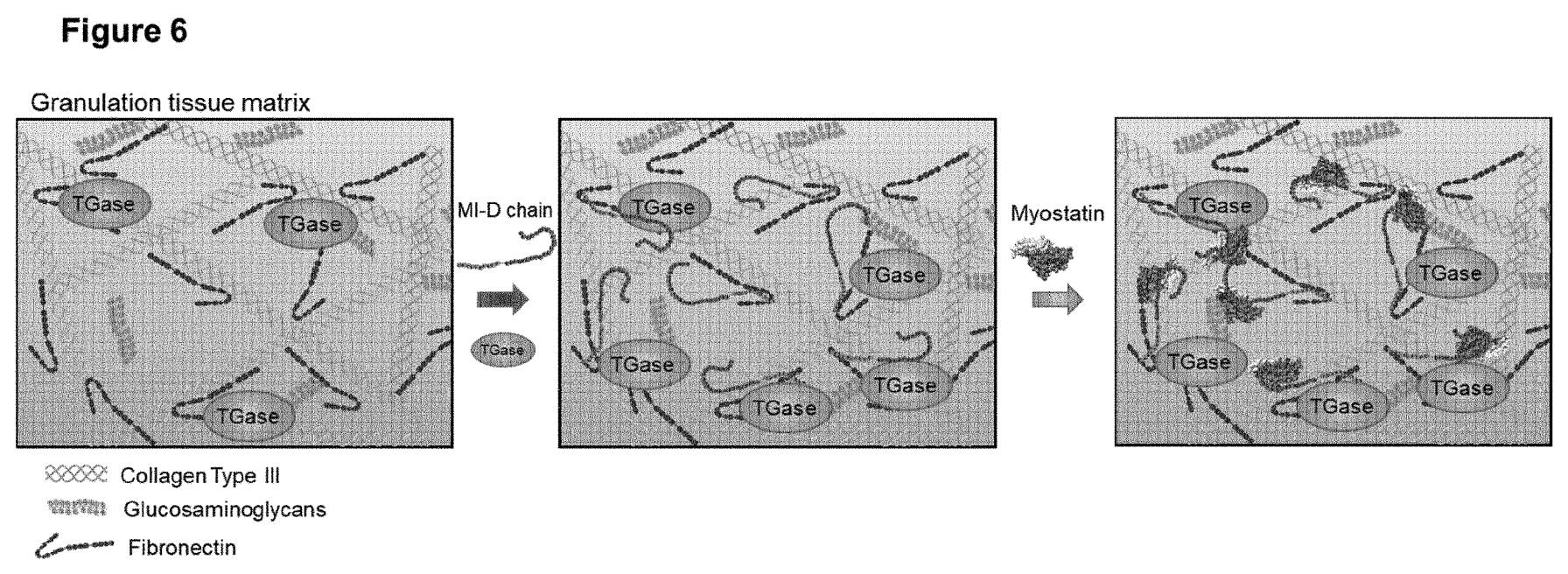

FIG. 6: Illustration of the in situ delivery of MI-D chain to injured tissue. In the injured tissue, transglutaminase catalyzes the crosslinking of the MI with endogenous fibronectin on the ECM, resulting in local accumulation of the MI, thereby neutralizing upregulated myostatin at the wound site.

REFERENCES

Figure 1:
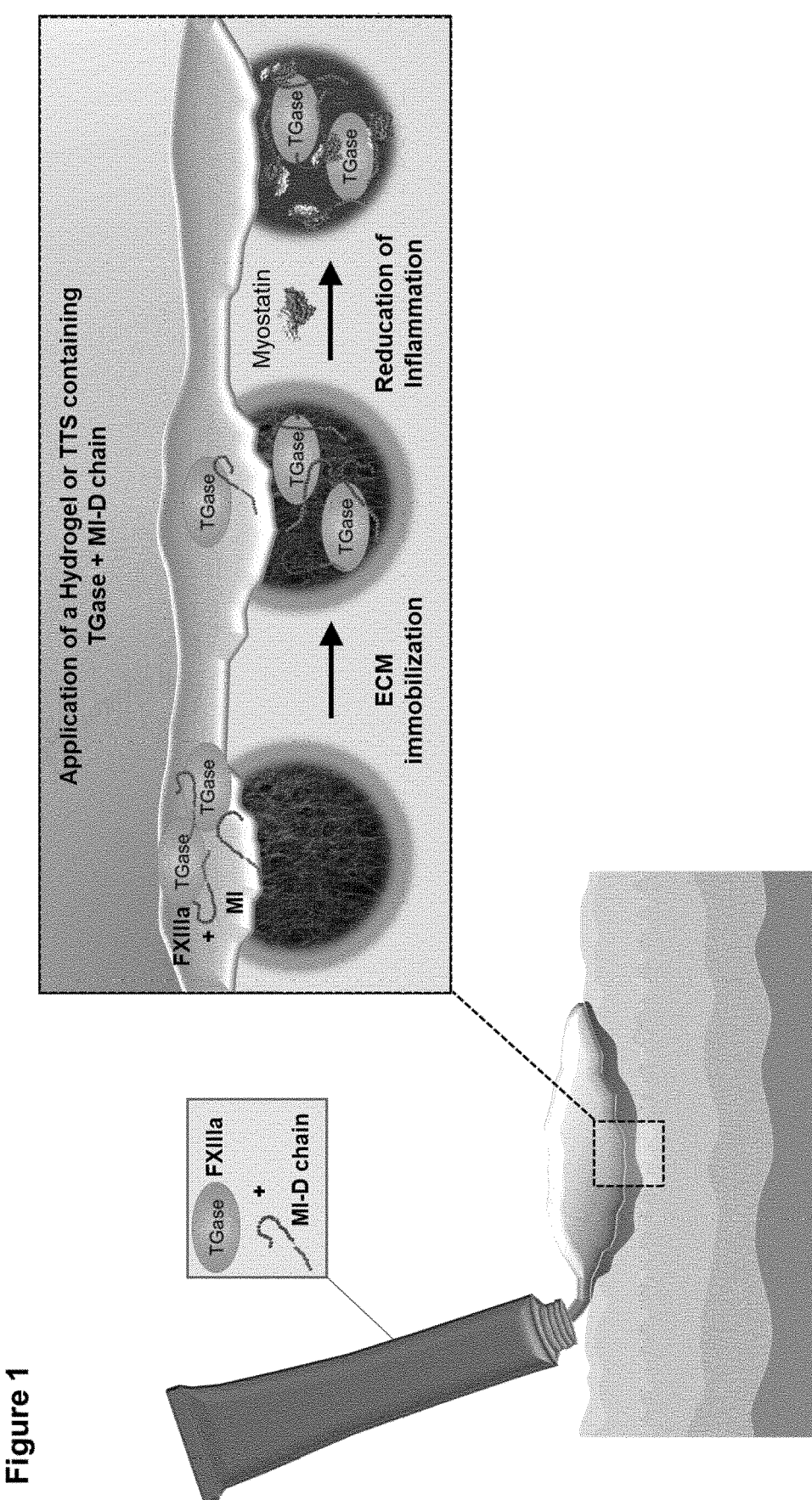
FIG. 1: By topical application of the myostatin inhibitor together with the crosslinking enzyme in one hydrogel/TTS onto the wound, the organism is supported in the recovery process.
Figure 2:
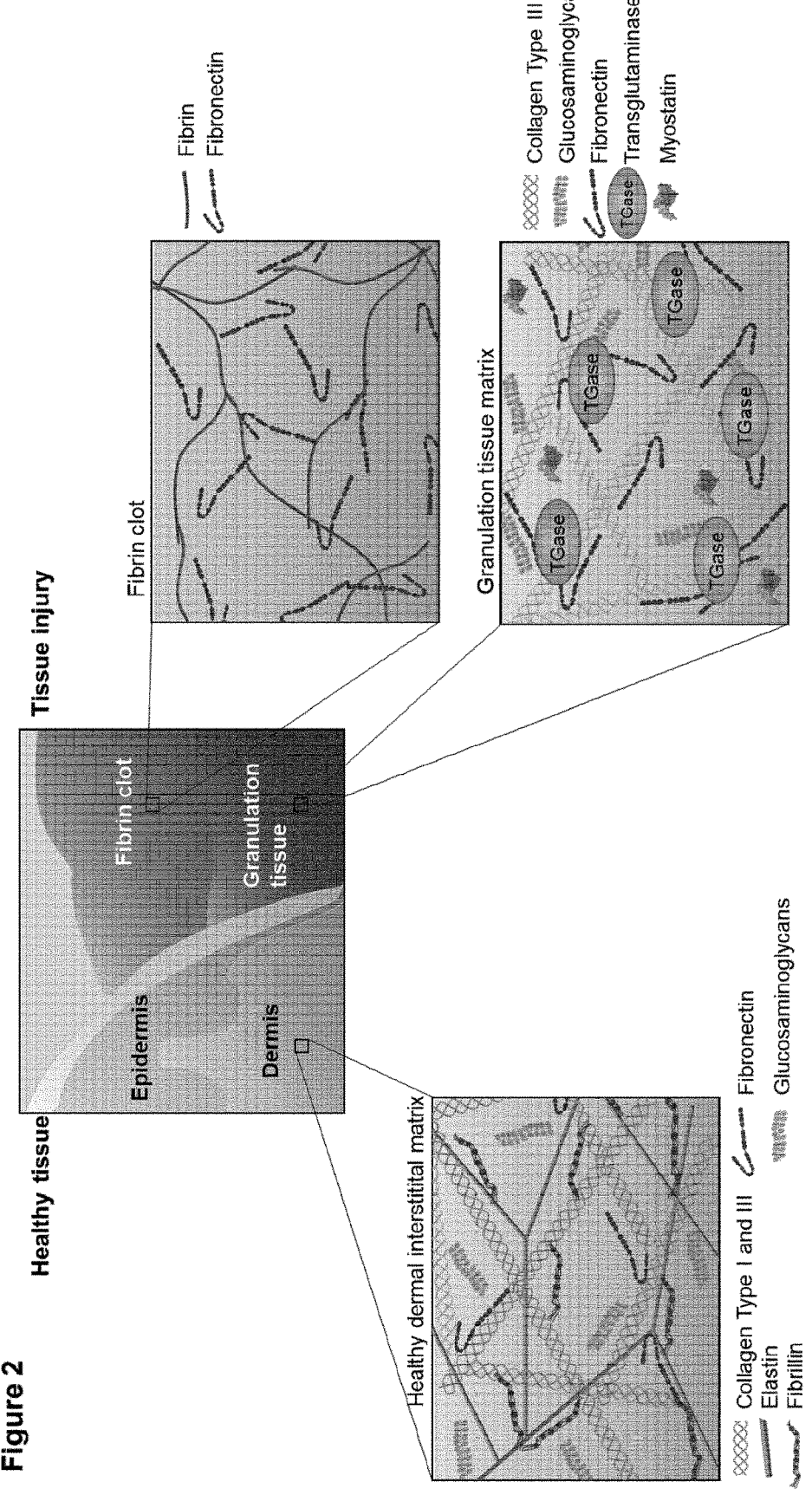
FIG. 2: ECM compositions in healthy skin and during wound healing.
Figure 3:
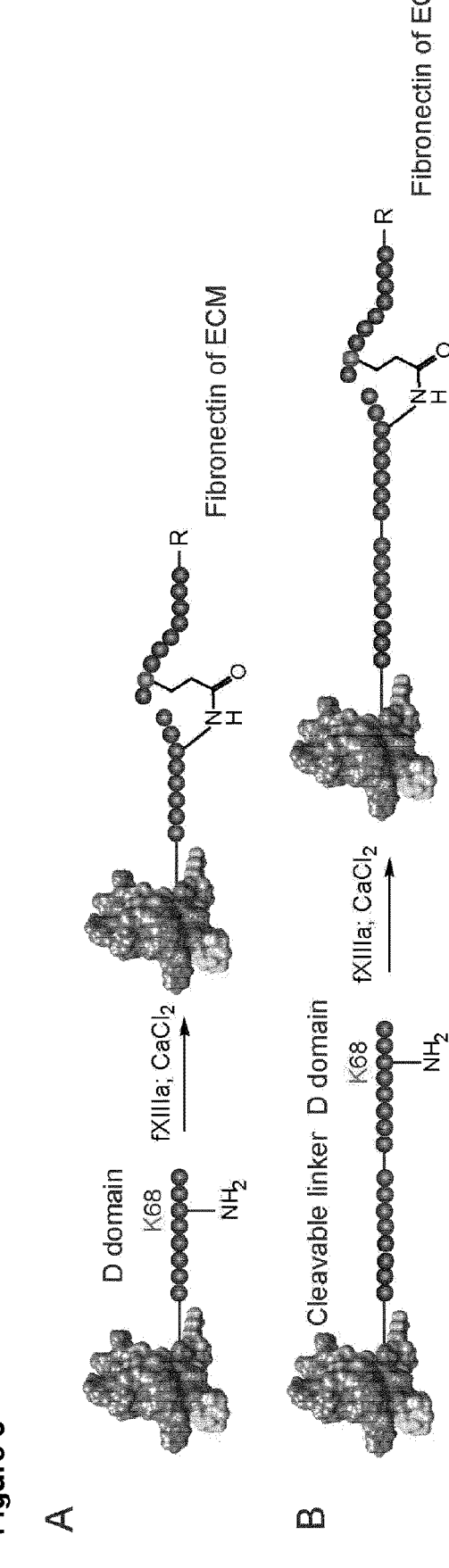
FIG. 3: Schematic illustration of in situ ECM immobilization of the myostatin inhibitor (MI) mediated by human fXIIIa. (A) In situ MI immobilization on the ECM protein fibronectin through integration of IGF-I's D domain. (B) Integration of a protease cleavable linker (e.g. derived from collagen type I) to enable a faster release as response to matrix metalloproteinase upregulation in inflamed environment.
Figure 4:
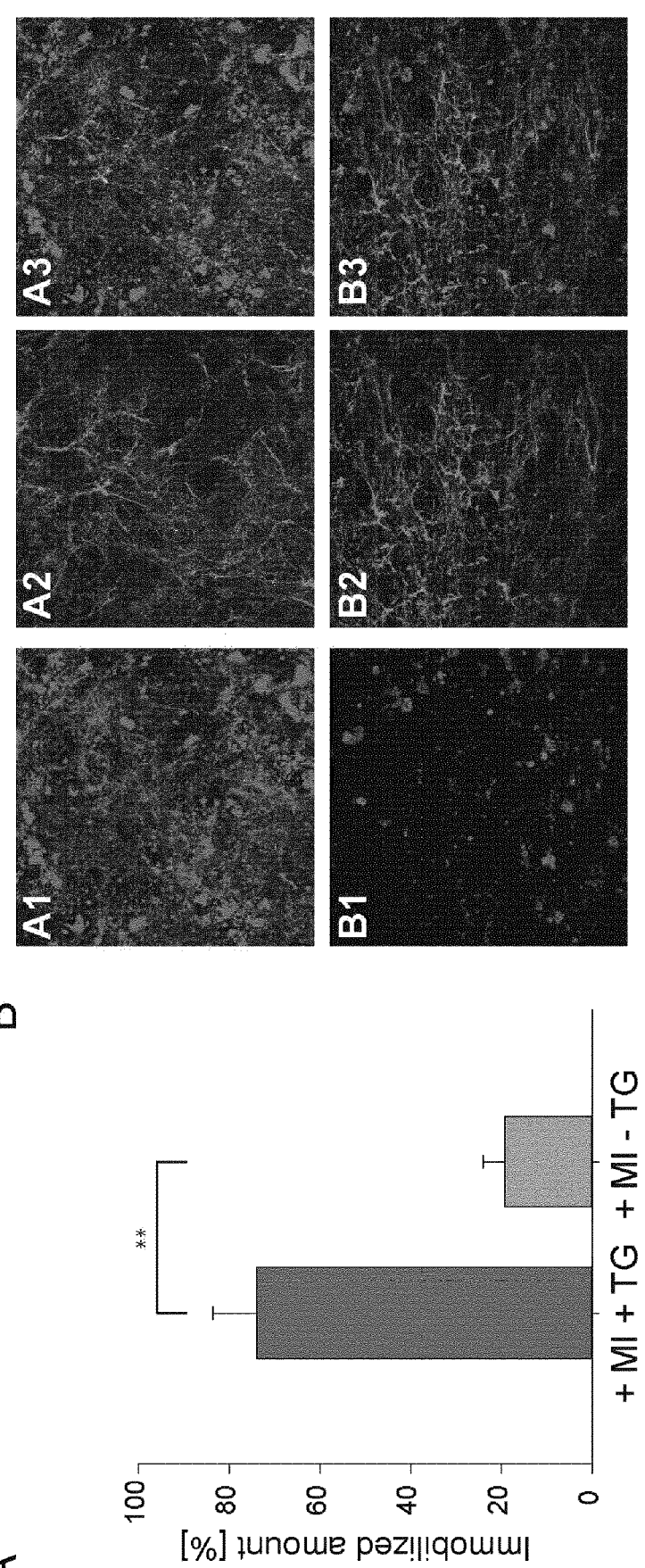
FIG. 4: Immobilization of the MI-D chain on decellularized ECM. (A) Coupling efficacy in presence and absence of TG. (B) Confocal Laser Scanning Microscopy images of MI labeled with Atto594-maleimide on ECM in presence (panels A) and absence (panels B) of FXIIIa. The red fluorescence (1) shows immobilized MI and the green fluorescence (2) an antibody-staining of fibronectin (3 represents the overlay). (C) Amount of free myostatin after exposure to ECM with immobilized MI under different conditions measured by ELISA. (D) Bioactivity of MI immobilized on ECM determined by differentiation of myoblasts in presence of myostatin-containing medium and MI bound on ECM in presence or absence of TG.
Figure 4:
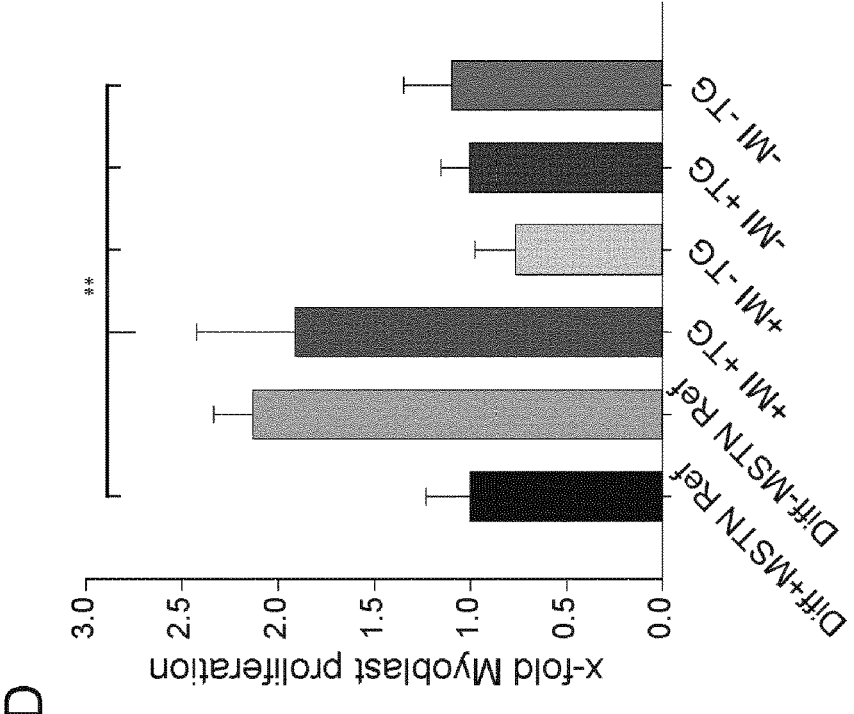
Figure 4:
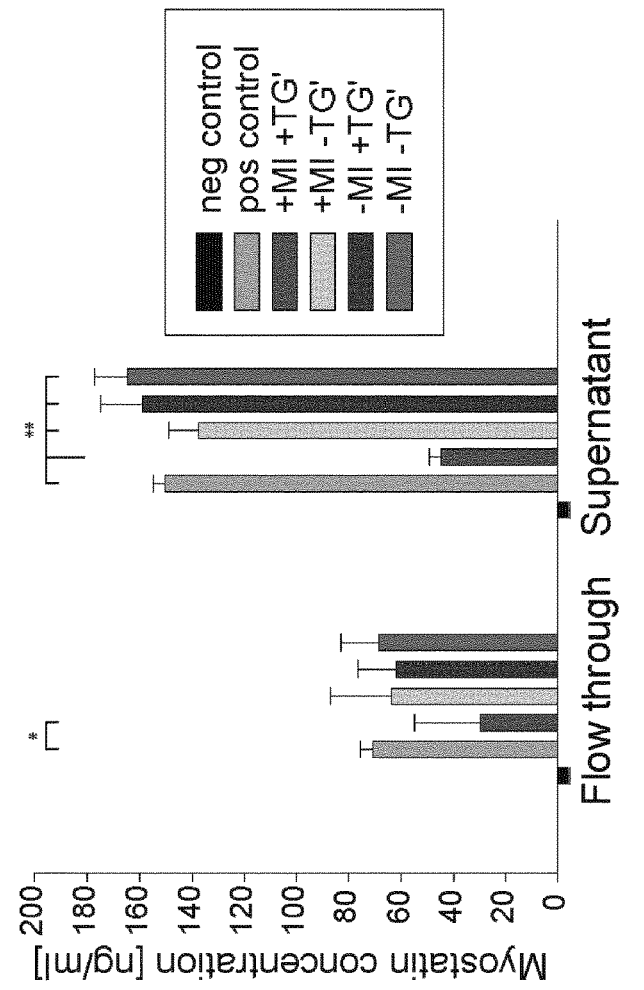
Figure 5:
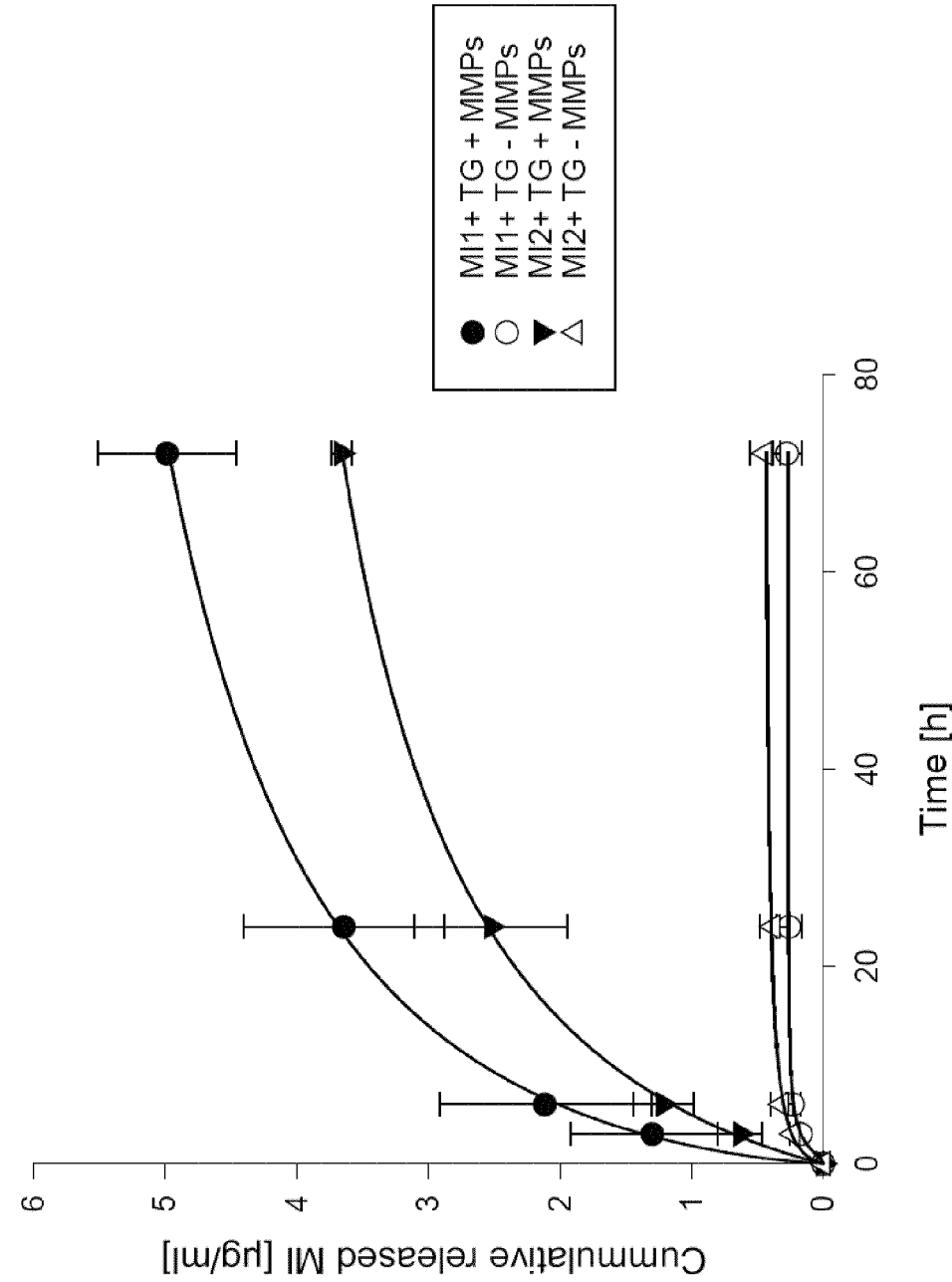
FIG. 5: (A) Release kinetics of MI modified with a PCL—responding to elevated MMP levels—and the D chain for immobilization on ECM ("MI1") in comparison to MI modified with the D chain at the C-terminus for direct immobilization on ECM ("MI2"). The MI was labelled with a fluorescent dye before immobilization on the ECM and the release of MI exposed to MMP-1, -8, -9 and -13 for different periods of time was analyzed by HPLC with fluorescence detection. (B) Bioactivity of released MI determined by myoblast proliferation in presence of myostatin and MI after release from ECM triggered by MMPs.
Figure 5:
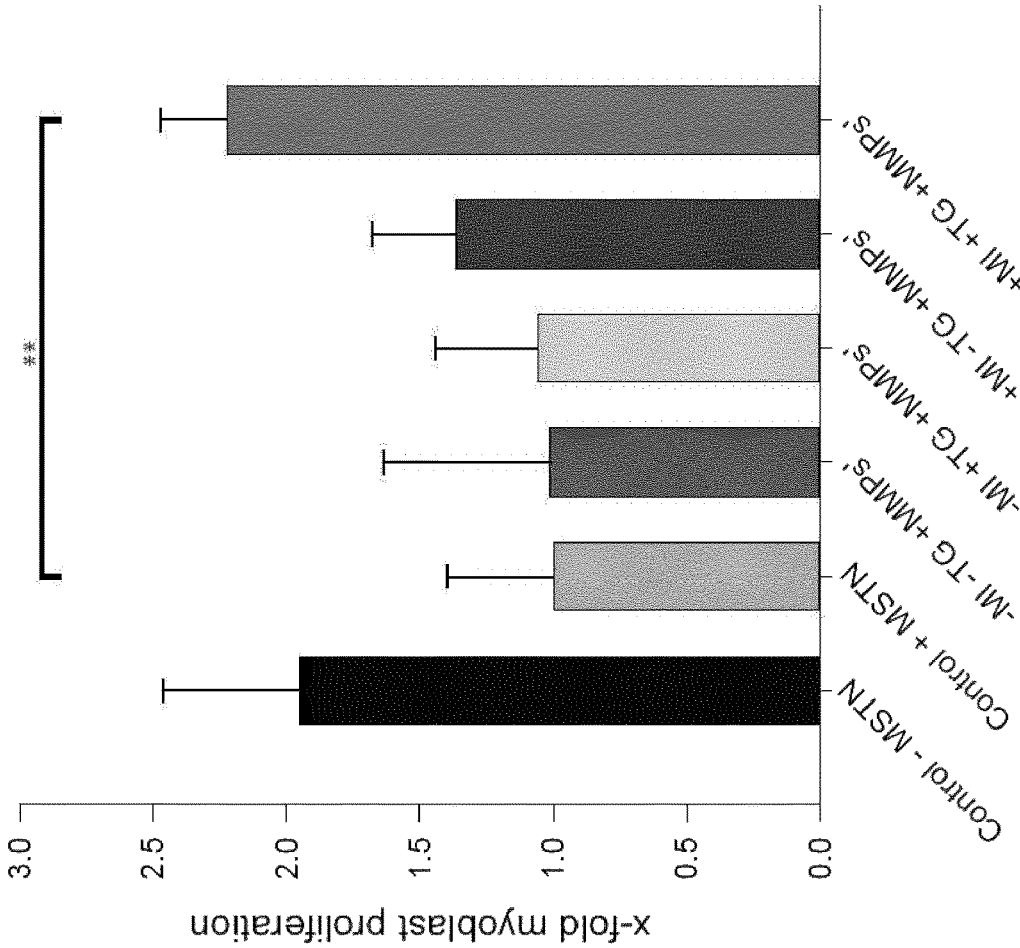

[1] A. C. Braun, M. Gutmann, R. Ebert, F. Jakob, H. Gieseler, T. Lühmann, L. Meinel, Matrix Metalloproteinase Responsive Delivery of Myostatin Inhibitors, Pharmaceutical Research, (2016).

[2] T. Lühmann, L. Meinel, Nanotransporters for drug delivery, Current Opinion in Biotechnology, 39 (2016) 35-40.

[3] K. Lee, E. A. Silva, D. J. Mooney, Growth factor delivery-based tissue engineering: general approaches and a review of recent developments, Journal of The Royal Society Interface, 8 (2011) 153-170.

[4] P. S. Briquez, J. A. Hubbell, M. M. Martino, Extracellular Matrix-Inspired Growth Factor Delivery Systems for Skin Wound Healing, Advances in Wound Care, 4 (2015) 479-489.

[5] M. Griffin, R. Casadio, C. M. Bergamini, Transglutaminases: nature's biological glues, Biochemical Journal, 368 (2002) 377-396.

[6] H. F. Upchurch, E. Conway, M. K. Patterson, M. D. Maxwell, Localization of cellular transglutaminase on the extracellular matrix after wounding: Characteristics of the matrix bound enzyme, Journal of Cellular Physiology, 149 (1991) 375-382.

[7] T. J. Sanborn, P. B. Messersmith, A. E. Barron, In situ crosslinking of a biomimetic peptide-PEG hydrogel via thermally triggered activation of factor XIII, Biomaterials, 23 (2002) 2703-2710.

[8] Z.-Y. Zhang, P. Shum, M. Yates, P. B. Messersmith, D. H. Thompson, Formation of Fibrinogen-Based Hydrogels Using Phototriggerable Diplasmalogen Liposomes, Bioconjugate Chemistry, 13 (2002) 640-646.

[9] A. Sala, M. Ehrbar, D. Trentin, R. G. Schoenmakers, J. Voros, F. E. Weber, Enzyme Mediated Site-Specific Surface Modification, Langmuir, 26 (2010) 11127-11134.

[10] J. C. Schense, J. A. Hubbell, Cross-linking exogenous bifunctional peptides into fibrin gels with factor XIIIa, Bioconjugate Chemistry, 10 (1999) 75-81.

[11] D. J. Fieten, The Effect of a Myostatin Antagonist on the Healing of Burn Wounds in Skin, in, University of Waikato, Hamilton, New Zealand, 2009.

[12] M. M. Martino, P.S. Briquez, E. Güç, F. Tortelli, W. W. Kilarski, S. Metzger, J. J. Rice, G. A. Kuhn, R. Müller, M. A. Swartz, J. A. Hubbell, Growth Factors Engineered for Super-Affinity to the Extracellular Matrix Enhance Tissue Healing, Science, 343 (2014) 885-888.

[13] R. P. McDonagh, J. McDonagh, T. E. Petersen, H. C. ThØgersen, K. Skorstengaard, L. Sottrup-Jensen, S. Magnusson, Amino acid sequence of the factor XIIIa acceptor site in bovine plasma fibronectin, FEBS Letters, 127 (1981) 174-178.

[14] S. M. Früh, P. R. Spycher, M. Mitsi, M. A. Burkhardt, V. Vogel, I. Schoen, Functional Modification of Fibronectin by N-Terminal FXIIIa-Mediated Transamidation, ChemBioChem, 15 (2014) 1481-1486.

The invention claimed is:

1. A synthetic compound suitable for transglutaminase-mediated binding or attachment or incorporation of a therapeutic and/or diagnostic molecule into an extracellular matrix or a synthetic extracellular matrix component, wherein said compound comprises (a) at least one anchor domain and (b) at least one second domain, wherein said second domain possesses therapeutic and/or preventive activity, wherein said anchor domain is the isolated D domain of Insulin Growth Factor-1 (IGF-I) as depicted in SEQ ID NO: 1, wherein said isolated D domain does not comprise the growth factor activity of IGF-I, wherein said anchor domain is capable of binding to an extracellular matrix or a synthetic extracellular matrix component;

wherein said second domain is directly or indirectly linked to the anchor domain, and wherein said second domain comprises the amino acid sequence as defined in SEQ ID NO: 12.

2. The synthetic compound according to claim 1, wherein the second domain is selected from the group consisting of a binder of myostatin and a protein.

3. The synthetic compound according to claim 1, wherein said compound further comprises a cleavable linker between the anchor domain and the at least one second domain, wherein the linker has an amino acid sequence as depicted in SEQ ID NO: 13.

4. A pharmaceutical composition or formulation comprising a synthetic compound as defined in claim 1.

5. The pharmaceutical composition or formulation according to claim 4, wherein said composition or formulation is suitable for localized administration.

6. The pharmaceutical composition according to claim 4, wherein said pharmaceutical composition is suitable for administration selected from transdermal, ophthalmic, nasal, otologic, enteral, pulmonal, urogenital, subcutaneous, intra-articular, intravenous, intracardiac, intramuscular, intraosseous and intraperitoneal administration.

7. The synthetic compound according to claim 1, wherein said second domain inhibits and/or reduces and/or suppresses the activity of human myostatin.

8. The synthetic compound according to claim 2, wherein the second domain is a myostatin inhibitor or a myostatin suppressor.

9. A device comprising a synthetic compound as defined in claim 1, wherein said device is selected from the group consisting of patches, implants, scaffolds, porous vascular grafts, stents, and/or wound dressings.

10. The device according to claim 9, wherein the device is suitable as a delivery system for immediate and/or sustained release of said compound.

11. The device according to claim 9, wherein said device is made of biocompatible fleece, hydrocolloid, polyacrylate, alginate, hydrogel, or foam, and/or an artificially produced tissue, bone-replacement, polymer network, fibrin, collagen, elastin, hyaluronic acid or silk protein.

\* \* \* \* \*

SEQUENCE LISTING

```
<160> NUMBER OF SEQ ID NOS: 14

<210> SEQ ID NO 1
<211> LENGTH: 8
<212> TYPE: PRT
<213> ORGANISM: Homo sapiens

<400> SEQUENCE: 1

Pro Leu Lys Pro Ala Lys Ser Ala
1               5

<210> SEQ ID NO 2
<211> LENGTH: 7
<212> TYPE: PRT
<213> ORGANISM: Homo sapiens

<400> SEQUENCE: 2

Leu Lys Pro Ala Lys Ser Ala
1               5

<210> SEQ ID NO 3
<211> LENGTH: 6
```

```
<212> TYPE: PRT
<213> ORGANISM: Homo sapiens

<400> SEQUENCE: 3

Lys Pro Ala Lys Ser Ala
1               5

<210> SEQ ID NO 4
<211> LENGTH: 5
<212> TYPE: PRT
<213> ORGANISM: Homo sapiens

<400> SEQUENCE: 4

Pro Ala Lys Ser Ala
1               5

<210> SEQ ID NO 5
<211> LENGTH: 4
<212> TYPE: PRT
<213> ORGANISM: Homo sapiens

<400> SEQUENCE: 5

Ala Lys Ser Ala
1

<210> SEQ ID NO 6
<211> LENGTH: 8
<212> TYPE: PRT
<213> ORGANISM: Mus musculus

<400> SEQUENCE: 6

Pro Leu Lys Pro Thr Lys Ala Ala
1               5

<210> SEQ ID NO 7
<211> LENGTH: 7
<212> TYPE: PRT
<213> ORGANISM: Mus musculus

<400> SEQUENCE: 7

Leu Lys Pro Thr Lys Ala Ala
1               5

<210> SEQ ID NO 8
<211> LENGTH: 6
<212> TYPE: PRT
<213> ORGANISM: Mus musculus

<400> SEQUENCE: 8

Lys Pro Thr Lys Ala Ala
1               5

<210> SEQ ID NO 9
<211> LENGTH: 5
<212> TYPE: PRT
<213> ORGANISM: Mus musculus

<400> SEQUENCE: 9

Pro Thr Lys Ala Ala
1               5

<210> SEQ ID NO 10
<211> LENGTH: 4
<212> TYPE: PRT
<213> ORGANISM: Mus musculus
```

```
<400> SEQUENCE: 10

Thr Lys Ala Ala
1

<210> SEQ ID NO 11
<211> LENGTH: 8
<212> TYPE: PRT
<213> ORGANISM: Homo sapiens

<400> SEQUENCE: 11

Asn Gln Glu Gln Val Ser Pro Leu
1               5

<210> SEQ ID NO 12
<211> LENGTH: 20
<212> TYPE: PRT
<213> ORGANISM: Homo sapiens

<400> SEQUENCE: 12

Val Ala Thr Gln Gly Gln Cys Thr Arg Trp Pro Trp Met Cys Pro Pro
1               5                   10                  15

Gln Gly Trp Gly
            20

<210> SEQ ID NO 13
<211> LENGTH: 8
<212> TYPE: PRT
<213> ORGANISM: Artificial Sequence
<220> FEATURE:
<223> OTHER INFORMATION: Artificial linker sequence

<400> SEQUENCE: 13

Gly Pro Gln Gly Ile Ala Gly Gln
1               5

<210> SEQ ID NO 14
<211> LENGTH: 11
<212> TYPE: PRT
<213> ORGANISM: Homo sapiens

<400> SEQUENCE: 14

Tyr Cys Ala Pro Leu Lys Pro Ala Lys Ser Ala
1               5                   10
```